United States Patent [19]

Kamiya et al.

[11] 4,215,043
[45] Jul. 29, 1980

[54] BICYCLOMYCIN DERIVATIVES

[75] Inventors: Takashi Kamiya, Suita; Shizuo Maeno, Osaka; Yoshihiko Kitaura, Suita, all of Japan

[73] Assignee: Fujisawa Pharmaceutical Co., Ltd., Osaka, Japan

[21] Appl. No.: 732,930

[22] Filed: Oct. 15, 1976

[30] Foreign Application Priority Data

Oct. 20, 1975 [GB] United Kingdom ............... 42912/75

[51] Int. Cl.² .......................................... C07D 498/06
[52] U.S. Cl. .......................... 260/239.3 B; 260/243.3; 424/250
[58] Field of Search ................. 260/268 BC, 268 DK, 260/239.3 B

[56] References Cited

PUBLICATIONS

Kamiya et al., *J. Antibiotics*, vol. 25 (1972), pp. 576–581.

*Primary Examiner*—Paul M. Coughlan, Jr.
*Attorney, Agent, or Firm*—Dayton R. Stemple, Jr.

[57] ABSTRACT

Bicyclomycin derivatives having the general formula:

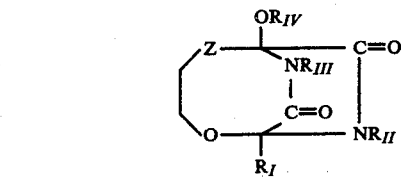

wherein $R_I$ is

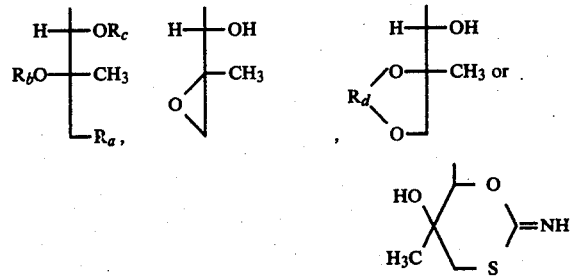

$R_{II}$ and $R_{III}$ are hydrogens or aliphatic, $R_{IV}$ is hydrogen, aliphatic, acyl, or aliphatic heterocyclic, and Z is

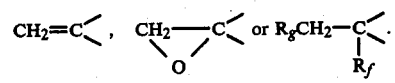

2 Claims, No Drawings

BICYCLOMYCIN DERIVATIVES

The present invention is concerned with new bicyclomycin derivatives, which are active against microorganisms and are also useful as intermediates for preparing pharmaceutical compounds having anti-microbial activities, and with the preparation thereof.

The new bicyclomycin derivatives according to the present invention are compounds of the general formula:

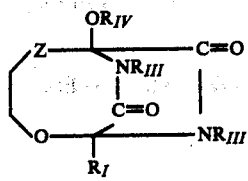
(I)

wherein $R_I$ is a grouping of the general formula:

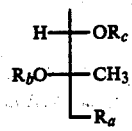

in which $R_a$ is a residue of nucleophile, organic sulphonyloxy, hydroxy, alkoxy, aralkoxy, acyloxy or an aliphatic heterocyclic oxy, $R_b$ is a hydrogen atom or an aliphatic hydrocarbon radical, and $R_c$ is a hydrogen atom or an aliphatic hydrocarbon radical or an acyl or aliphatic heterocyclic radical:

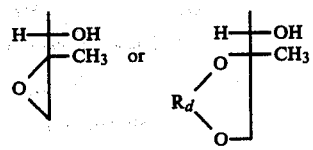

in which $R_d$ is an alkylidene or aralkylidene radical, or

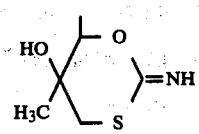

$R_{II}$ and $R_{III}$, which can be the same or different, are hydrogen atoms or aliphatic hydrocarbon radicals, $R_{IV}$ is a hydrogen atom or an aliphatic hydrocarbon radical or an acyl radical or an aliphatic heterocyclic radical, and Z is

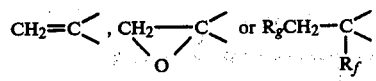

in which $R_g$ is a nucleophilic radical or a halogen atom; and $R_f$ is a hydrogen or halogen atom or a hydroxyl group, with the proviso that when $R_I$ is

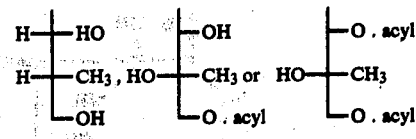

and $R_{II}$, $R_{III}$ and $R_{IV}$ are hydrogen, then Z is

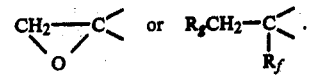

The new bicyclomycin derivatives (I) according to the present invention can be prepared by various methods, which can conveniently be illustrated by the following equations:

(1) Process 1.

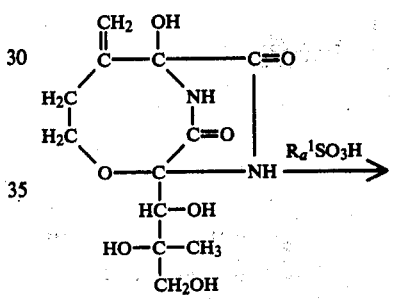

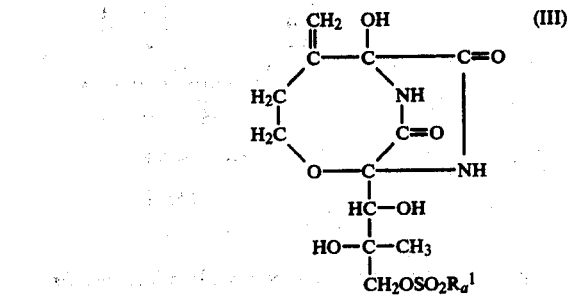

in which $R_a^1$ is an alkyl or aryl radical.

(2) Process 2.

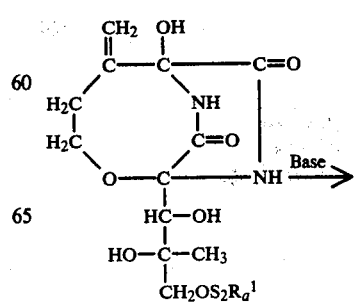

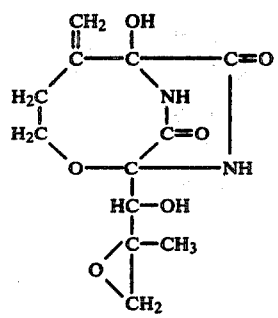 (IV)

in which $R_a{}^1$ is an alkyl or aryl radical.

(3) Process 3.

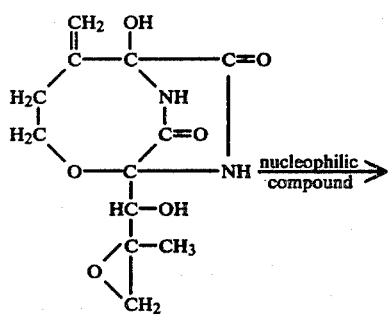

in which $R_a{}^2$ is the residue of a nucleophilic compound.

(4) Process 4.

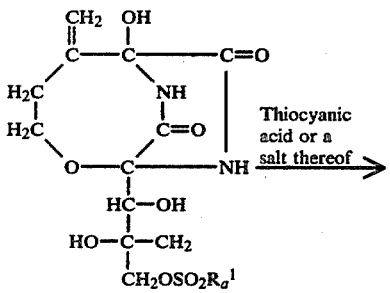 (III)

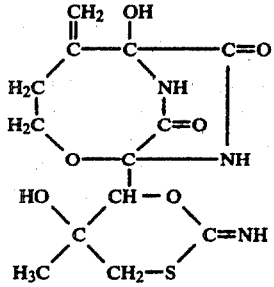 (VI)

in which $R_a{}^1$ is an alkyl or aryl radical.

(5) Process 5.

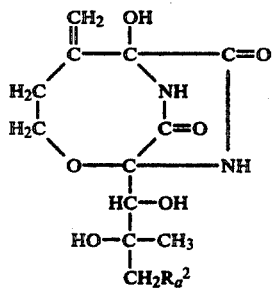 (IV)

(VII)

in which $R_a{}^3$ is an alkyl, aralkyl or aliphatic heterocyclic radical and $R_c{}^1$ and $R_{IV}{}^1$, which may be the same or different, are hydrogen atoms or alkyl, aralkyl or aliphatic heterocyclic radicals.

(6) Process 6.

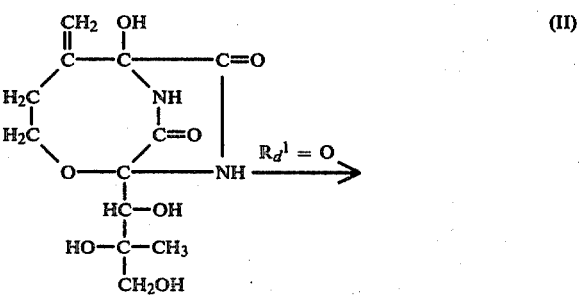 (II)

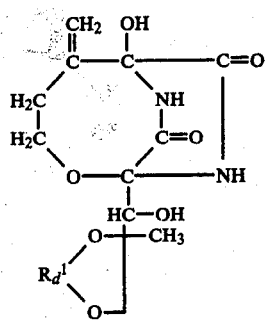  (VIII)

in which $R_d{}^1$ is an alkylidene or aralkylidene radical.

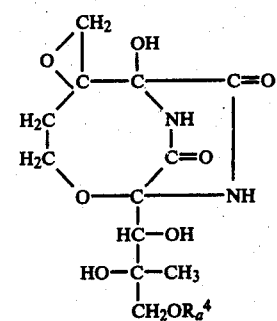  (XI)

in which $R_a{}^4$ is a hydrogen atom or an acyl radical.

(7) Process 7.

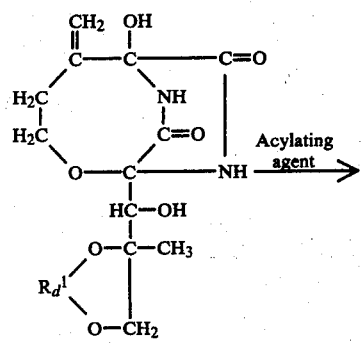

in which $R_d{}^1$ is an alkylidene or aralkylidene radical and $R_c{}^2$ and $R_{IV}{}^2$, which may be the same or different, are hydrogen atoms or acyl radicals, with the proviso that at least one of them is an acyl radical.

(8) Process 8.

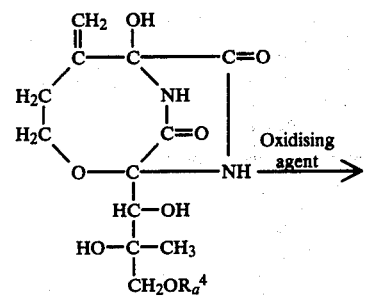

(9) Process 9.

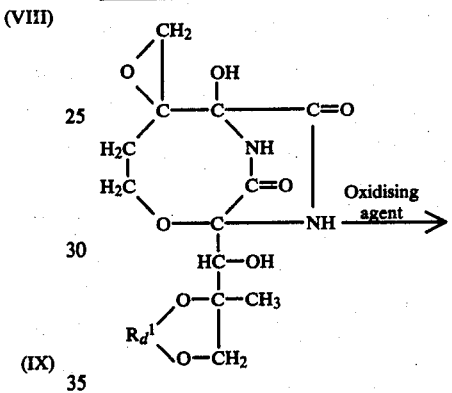

in which $R_a{}^1$ is an alkylidene or aralkylidene radical.

(10) Process 10.

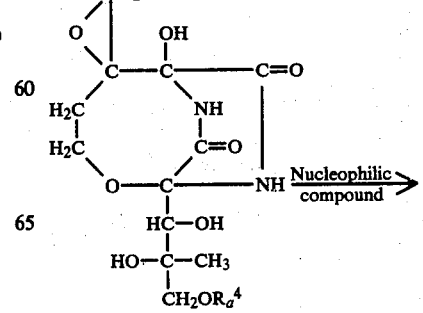

-continued (XIII)

in which $R_a^4$ is a hydrogen atom or an acyl radical, $R_f^1$ is a hydrogen atom or a hydroxyl group and $R_g^1$ is a nucleophilic radical.

(11) Process 11.

(XII)

$\xrightarrow{\text{Nucleophilic compound}}$ (XIV)

in which $R_d^1$ is an alkylidene or aralkylidene radical, $R_f^2$ is a hydrogen atom or a hydroxyl group and $R_g^2$ is a nucleophilic radical.

(12) Process 12.

(XV)

$\xrightarrow{\text{elimination of a protective group on a hydroxyl group}}$

-continued (XVI)

in which $R_h$ is a protective group on a hydroxyl group and $R_b^1$, $R_c^3$, $R_{II}^1$, $R_{III}^1$ and $R_{IV}^3$, which may be the same or different, are hydrogen atoms or aliphatic hydrocarbon radicals.

(13) Process 13.

(X)

$\xrightarrow{\text{Halogenating agent}}$ (XVIII)

in which $R_a^4$ is a hydrogen atom or an acyl radical and $R_f^3$ and $R_g^3$, which can be the same or different, are halogen atoms.

(14) Process 14.

(XIX)

$\xrightarrow{\text{Alkylating agent}}$

-continued

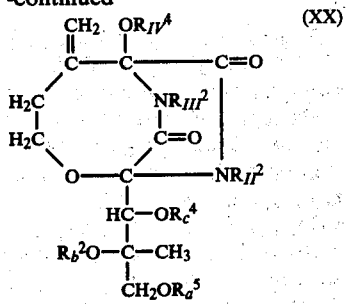

in which $R_a{}^5$ is a hydrogen atom or an aralkyl or acyl radical and $R_b{}^2$, $R_c{}^4$, $R_{II}{}^2$, $R_{III}{}^2$ and $R_{IV}{}^4$, which can be the same or different, are hydrogen atoms or aliphatic hydrocarbon radicals, with the proviso that one of them is an aliphatic hydrocarbon radical.

(15) Process 15.

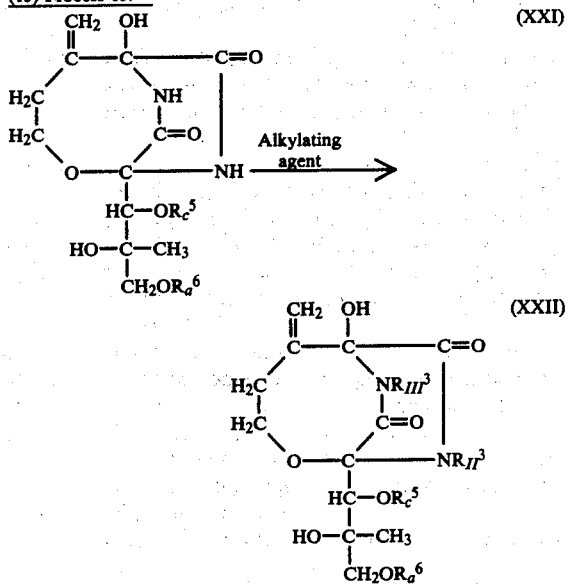

in which $R_a{}^6$ and $R_c{}^5$, which may be the same or different, are acyl radicals and $R_{II}{}^3$ and $R_{III}{}^3$, which may be the same or different, are hydrogen atoms or aliphatic hydrocarbon radicals, with the proviso that one of them is an aliphatic hydrocarbon radical.

Examples of the definitions for the symbols used in the above-given general formulae, include the following:

With respect to the compounds of general formula (I):

Examples of organic sulphonyloxy for $R_a$ include alkane-sulphonyloxy (e.g., methanesulphonyloxy, ethanesulphonyloxy, etc.) and arene sulphonyloxy (e.g. benzenesulphonyloxy, toluenesulphonyloxy, chlorobenzenesulphonyloxy, etc.) and the like.

Alkoxy for $R_a$ includes substituted and unsubstituted alkoxy radicals.

Examples of alkoxy for $R_a$ include $C_1$–$C_6$ and preferably $C_1$–$C_4$ alkoxy radicals (e.g., methoxy, ethoxy, n-propoxy, isopropoxy, n-butoxy, isobutoxy, pentoxy, hexyloxy, etc.). Examples of substituents in the substituted alkoxy radicals include alkanoyl (e.g., acetyl, n-propionyl, n-butyryl, isopropionyl, hexanoyl, etc.), aroyl (e.g., benzoyl, toluoyl, xyloyl, naphthoyl, etc.), alkoxycarbonyl (e.g., methoxycarbonyl, ethoxycarbo-nyl, etc.), substituted and unsubstituted carbamoyl (e.g., carbamoyl, N-methylcarbamoyl, N-ethylcarbamoyl, N,N-diethylcarbamoyl, etc.), substituted and unsubstituted amino (e.g., amino, methylamino, acetamido, benzamido, ethoxycarbonylamino, t-butoxycarbonylamino, benzyloxycarbonylamino, N,N-diethylamino, etc.) and the like.

Examples of aralkoxy for $R_a$ include benzyloxy, phenethyloxy, trityloxy, phenylpropoxy, phenylbutoxy and the like.

Examples of the acyl moiety in acyloxy radicals for $R_a$ can be the same as those given hereinafter for acyl for $R_c$, $R_{IV}{}^2$, $R_a{}^4$, $R_a{}^5$, $R_a{}^6$ and $R_c{}^5$.

With respect to the compounds of general formulae (I), (V), (XIII) and (XIV):

Examples of nucleophilic radicals in the definitions for $R_a$, $R_g$, $R_a{}^2$, $R_g{}^1$ and $R_g{}^2$ include radicals of the following nucleophilic compounds:

(a) S-nucleophiles:

Hydrogen sulphide, thiocyanic acid, lower alkylsubstituted thioureas (e.g., N-methylthiourea, N,N,N'-triethylthiourea, etc.) diarylthioureas (e.g. diphenylthiourea, etc.), diheterocyclic thioureas (e.g., N,N-difurylthiourea, etc.), thio(lower)alkaneamides (e.g., thioacetamide, etc.), aromatic thioamides (e.g., thiobenzamide, etc.), lower alkanethiols (e.g., methanethiol, ethanethiol, etc.), lower alkoxycarbonyl-substituted lower alkanethiols (e.g., methoxycarbonyl-methanethiol, ethoxycarbonyl-methanethiol, etc.), aromatic thiols (e.g., thiophenol, etc.), heterocyclic thiols, such as lower alkylthiadiazolethiols (e.g., methylthiadiazolethiol, etc.), thio(lower)alkanoic acids (e.g., thioacetic acid, etc.), aromatic thiocarboxylic acids (e.g., thiobenzoic acid, etc.), dithiocarbonic acids, such as lower alkyl dithiocarbonic acid (e.g., dithioacetic acid, dithiopropionic acid, etc.) and ar(lower)alkyl dithiocarbonic acids (e.g., benzyl dithiocarbonic acid, etc.).

(b) N-nucleophiles:

Ammonia, aliphatic amines, such as mono(or di)-lower alkylamines (e.g., methylamine, diethylamine, etc.), aromatic amines (e.g., aniline, toluidine, nitroaniline, etc.), aminobenzoic acid, benzenesulphonamide, phthalimide and succinimide.

(c) O-nucleophiles:

Aliphatic alcohols, such as lower alkanols (e.g., methanol, ethanol, propanol, etc.), phenols ar(lower)alkanols (e.g., benzyl alcohol, phenethyl alcohol, etc.), lower alkanoic acids (e.g., acetic acid, etc.) and aromatic carboxylic acids (e.g., benzoic acid, etc.).

With respect to the compounds of general formulae (III) and (VII):

Examples of alkyl in the definitions for $R_a{}^1 R_a{}^3$, $R_c{}^1$ and $R_{IV}{}^1$ include methyl, ethyl, npropyl, isopropyl, n-butyl, isobutyl, pentyl, hexyl and the like.

With respect to the compounds of general formula (III):

Examples of aryl in the definitions for $R_a{}^1$ include phenyl, naphthyl, xylyl, tolyl and the like.

With respect to the compounds of general formulae (VII) and (XIX):

Examples of aralkyl in the definitions for $R_a{}^3$, $R_a{}^5$, $R_c{}^1$ and $R_{IV}{}^1$ include benzyl, phenethyl, benzhydryl, trityl, phenylpropyl, phenylbutyl and the like.

With respect to the compounds of general formulae (I) and (VII):

Examples of aliphatic heterocyclic radicals for $R_a$, $R_a{}^3$, $R_c$, $R_c{}^1$, $R_{IV}$ and $R_{IV}{}^1$ include the radicals of 5- to 6-membered aliphatic heterocycles containing at least one oxygen or sulphur atom (e.g., tetrahydrofuranyl, tetrahydropyranyl, tetrahydrothiopyranyl, etc.).

With respect to the compounds of general formulae (I), (IX), (X), (XI), (XIII), (XVIII), (XIX) and (XXI):

Examples of acyl in the definitions for $R_c$, $R_{IV}{}^2$, $R_a{}^4$, $R_a{}^5$, $R_a{}^6$ and $R_c{}^5$ include aliphatic acyl, aromatic acyl and heterocyclic acyl radicals as follows:

aliphatic acyl, such as saturated or unsaturated aliphatic hydrocarbon carbonyl, for example, alkanoyl (e.g., acetyl, n-propionyl, n-butyryl, isobutyryl, valeryl, isovaleryl, pivaloyl, 2-ethylbutyryl, capropyl, palmitoyl, stearoyl, etc.) having 2 to 20 carbon atoms, and alkenoyl (e.g. acryloyl, meta-acryloyl, crotonoyl, oleoyl, linoleoyl, linolenoyl, etc.) having 2 to 20 carbon atoms; a saturated or unsaturated aliphaic cyclohydrocarbon carbonyl, for example, cycloalkane carbonyl (e.g., cyclohexane carbonyl) and cycloalkane carbonyl (e.g., cyclohexane carbonyl); or an aliphatic cyclohydrocarbn-substituted aliphatic hydrocarbon carbonyl, for example, cycloalkyl alkanoyl (e.g. cyclohexylacetyl, cyclohexylpropionyl, etc.) having 7 to 13 carbon atoms, the aliphatic hydrocarbon moiety of said aliphatic hydrocarbon acyl having a straight or branched chain and optionally interrupted by a hetero atom, such as an oxygen or sulphur atom (e.g. methoxyacetyl, methylthioacetyl, butylthoacetyl, methoxycarbonyl, ethoxycarbonyl, cyclohexylthioacetyl, etc.).

Aromatic acyl, such as aroyl radicals (e.g. benzoyl, toluoyl, xyloyl, naphthoyl, etc.) or aryl-substituted aliphatic hydrocarbon carbonyl, for example, aralkanoyl (e.g. phenylacetyl, phenylpropionyl, tropoyl, etc.) and aralkenoyl (e.g. cinnamoyl, etc.). The aliphatic hydrocarbon moiety (i.e. alkane or alkenemoiety) having up to 6 carbon atoms of said aryl-substituted aliphatic hydrocarbon carbonyl (i.e. aralkanoyl and aralkenoyl) may be interrupted by a hetero atom, such as an oxygen and sulphur atom (e.g. phenoxyacetyl, phenylthioacetyl, etc.); heterocyclic acyl, such as heterocyclic ring carbonyl, including monoheterocyclic and diheterocyclic rings, or benzene-fused heterocyclic ring carbonyl, the heterocyclic ring being 5- or 6-membered and containing at least one nitrogen, oxygen and/or sulphur hetero atom (e.g. nicotinoyl, isonicotinoyl, 2-furoyl, 2-thenoyl, benzofuroyl, benzothenoyl, etc.); or aliphatic hydrocarbon carbonyl (e.g. alkanoyl or alkenoyl) substituted by said heterocyclic ring or benzene-fused heterocyclic ring (e.g. 1H-(or 2H) tetrazolylacetyl, thienylacetyl, furylacetyl, 3-benzothioazolylacetyl, 2-oxo-3-benzothiazolylacetyl, 3-indolylacetyl, morpholinoacetyl, etc.) in which the aliphatic hydrocarbon moiety (i.e. alkane or alkene) can contain up to 6 carbon atoms (preferably up to 4 carbon atoms) and can be interrupted by a hetero atom, such as an oxygen and sulphur atom.

With respect to the compounds of general formulae (I), (VIII), (IX), (XII) and (XIV):

Examples of alkylidene in the definitions for $R_d$ and $R_d{}^1$ include $C_1$-$C_4$ and preferably $C_1$-$C_2$ (e.g. ethylidene, propylidene, butylidene and the like).

Examples of aralkylidene in the definitions for $R_d$ and $R_d{}^1$ include benzylidene, phenethylidene, salicylidene and the like.

With respect to the compounds of general formulae (I), (XV), (XVI), (XX) and (XXII):

Examples of aliphatic hydrocarbon radicals in the definitions for $R_b$, $R_c$, $R_{II}$, $R_{III}$, $R_{IV}$, $R_b{}^1$, $R_c{}^3$, $R_{II}{}^1$, $R_{III}{}^1$, $R_{IV}{}^3$, $R_b{}^2$, $R_c{}^4$, $R_{II}{}^2$, $R_{III}{}^2$, $R_{IV}{}^4$, $R_{II}{}^3$ and $R_{III}{}^3$ include alkyl, substituted alkyl, alkenyl and alkynyl radicals.

Examples of alkyl radicals include $C_1$-$C_6$ are preferably $C_1$-$C_4$ alkyl (e.g., methyl, ethyl, n-propyl, isopropyl, n-butyl, isobutyl, pentyl, hexyl, etc.).

Examples of substituents in substituted alkyl radicals include alkanoyl (e.g., acetyl, n-propionyl, n-butyryl, isopropionyl, hexanoyl, etc.), aryl (e.g. phenyl, naphthyl, xylyl, tolyl, etc.), aroyl (e.g. benzoyl, toluoyl, xyloyl, naphthoyl, etc.), alkoxycarbonyl (e.g. methoxycarbonyl, ethoxycarbonyl, etc.), substituted and unsubstituted carbonyl (e.g., carbonyl, N-methylcarbonyl, N-ethylcarbonyl, N,N-diethylcarbonyl, etc.), substituted and unsubstituted amino (e.g., amino, methylamino, acetamido, benzamido, ethoxycarbonylamino, t-butoxycarbonylamino, etc.) and the like.

Alkenyl radicals include $C_2$-$C_6$ and preferably $C_2$-$C_4$ alkenyl (e.g., vinyl, propenyl, isopropenyl, etc.).

Alkynyl radicals include $C_2$-$C_6$ and preferably $C_2$-$C_4$ alkynyl (e.g., ethynyl, 2-propynyl, etc.).

With respect to the compounds of general formulae (I) and (XVIII):

Examples of halogen in the defintions for $R_f$, $R_g$, $R_f{}^3$ and $R_g{}^3$ include chlorine, bromine and iodine.

With respect to the compounds of general formula (XV):

Examples of protective groups on the hydroxyl groups in the definitions for $R_h$ include the conventional ones, such as aralkyl (e.g., benzhydryl, trityl, etc.), and 5- or 6-membered aliphatic heterocyclic radical containing at least an oxygen or sulphur atom (e.g., tetrahydropyranyl, tetrahydrofuranyl, tetrahydrothiopyranyl, etc.).

The processes for the preparation of the compounds of general formula (I) are explained hereinafter in detail:

In the processes of the present invention, it is to be understood that bicyclomycin and the acyl derivative thereof are used as starting compounds.

Bicyclomycin used as starting material in, for example, Process 1 and Process 6, is known as WS-4545 and is described in German Patent Specification No. 2,150,593.

The acyl derivatives of bicyclomycin used as starting materials in, for example, Process 8, Process 10 and Process 13, are also described in German Patent Specification No. 2,150,593.

(1) Process 1.

Preparation of organic sulphonyl esters of compounds (II):

(Example 8)

In this process, a compound (III) can be prepared by reacting a compound (II) with a sulphonic acid of the general formula $R_a$—$SO_3H$, wherein $R_a{}^1$ is an alkyl or aryl radical, or with a reactive derivative thereof, examples of alkyl and aryl for $R_a{}^1$ being given above.

Examples of reactive derivatives of the sulphonic acids include conventional ones, such as acid halides (e.g., acid chlorides, acid bromides, etc.), acid anhydrides acid azides and the like.

The reaction is usually carried out in a solvent. Examples of solvents include water, acetone, benzene, toluene, xylene, dioxan, dichloromethane, dimethylformamide, dimethyl sulphoxide, pyridine and N-methylmorpholine. However, any other solvents which do not have an adverse influence on the reaction may also be used.

The reaction is usually carried out at a reduced to a somewhat elevated temperature, which is selected in accordance with the solvent and the sulphonic acid or reactive derivative used, the reaction being preferably carried out with cooling or at an ambient temperature.

The reaction is preferably carried out in the presence of a base, such as an inorganic or an organic base. Examples of inorganic base include alkali metal hydroxides (e.g., sodium hydroxide, potassium hydroxide, etc.), alkaline earth metal hydroxides (e.g., magnesium hydroxide, calcium hydroxide, etc.), alkali metal carbonates (e.g., sodium carbonate, potassium carbonate, etc.), alkaline earth metal carbonates (e.g., calcium carbonate, magnesium carbonate, etc.), alkali metal bicarbonates (e.g., sodium bicarbonate, potassium bicarbonate, etc.), alkali metal hydrides (e.g., lithium hydride, sodium hydride, potassium hydride, etc.); silver oxide, ammonia, alkali metal amides (e.g., sodamide, lithium amide, etc.) and the like. Examples of organic bases include alkali metal alkoxides (e.g., sodium alkoxide, potassium alkoxide, etc.), alkane or aryl thiol metal salts (e.g., sodium methanethiolate, sodium ethanethiolate, sodium thiophenolate, etc.), organic amines (e.g., trimethylamine, triethylamine, dimethylaniline, pyridine, pycoline, lutidine, N-methyl-piperidine, etc.), and the like.

(2) Process 2:
Eliminative epoxidation of compounds (III):
(Examples 1–3)

In this process, compounds (IV) can be prepared by treating compounds (III) with a base.

Examples of bases include those given in the description of Process 1.

In this process, about equimolecular amounts of base to starting compound (III) are preferably employed.

The reaction is usually carried out in a solvent. Examples of solvents include water, methanol, ethanol, propanol, dioxan, tetrahydrofuran, dimethylformamide and the like.

The reaction temperature is not limited: the reaction is preferably carried out with cooling or at an elevated temperature.

(3) Process 3:
Cleavage of the epoxide ring of compounds (IV) with nucleophiles:
(Examples 4–7)

In this process, compounds (V) can be prepared by reacting compounds (IV) with a nucleophile.

Examples of nucleophiles are given above.

The reaction is usually carried out in a solvent. Examples of solvents include water, acetone, methanol, ethanol, ethyl acetate, dimethylformamide, dioxan, dichloromethane and the like but any other solvent which does not adversely influence the reaction can also be used.

In this reaction, a liquid nucleophile can also be used as the solvent for the reaction.

The reaction is preferably carried out in the presence of a base, examples of which are given in the description of Process 1.

The reaction temperature, which is not limited, is selected according to the nature of the nucleophile used.

(4) Process 4:
Reaction of compounds (III) with thiocyanic acid:
(Example 9)

In this process, compounds (VI) can be prepared by reacting compounds (III) with thiocyanic acid or a salt thereof.

Examples of salts of thiocyanic acid include the ammonium salts, alkali metal salts (e.g. the lithium, sodium and potassium salts, etc.), alkaline earth metal salts (e.g., magnesium and calcium salts, etc.), the copper salts, the silver salts and the like.

In this reaction, when thiocyanic acid is used, the reaction is preferably carried out in the presence of a base, examples thereof including those given in the description of Process 1.

The reaction is usually carried out in a solvent, for example water, methanol, ethanol, propanol, acetone, tetrahydrofuran, dimethylformamide and the like.

In the reaction, a liquid base can also be used as the solvent for the reaction.

The reaction temperature is not limited but the reaction is preferably carried out at ambient temperature or at an elevated temperature.

(5) Process 5:
Etherification of the hydroxy group of compounds (II):
(Examples 10, 12–13)

In this process, compounds (VII) can be prepared by reacting compounds (II) with etherifying agents of the general formula $R_h$–$Y_1$, wherein $R_h$ is an alkyl, aralkyl or aliphatic heterocyclic radical and $Y_1$ is an acid residue.

Examples of alkyl, aralkyl and aliphatic heterocyclic radicals for $R_h$ in the etherifying agent of the above-given general formula are illustrated above.

Examples of the acid residue for $Y_1$ include halogen, such as chlorine, bromine, iodine and the like.

Preferable examples of such etherifying agents include alkyl halides (e.g., methyl iodide, ethyl bromide, etc.), aralkyl halides (e.g., benzyl chloride, benzyl bromide, benzhydryl chloride, trityl chloride, etc.), aliphatic heterocyclic halides (e.g., 2-bromotetrahydrofuran, 2-chlorotetrahydropyran, 2-bromotetrahydrothiopyran, etc.), olefinic heterocycles (e.g., dihydrofuran, dihydrothiopyran, dihydropyran, etc.) and the like.

The reaction is usually carried out in a solvent, examples of which include pyridine, benzene, toluene, xylene, dioxan, tetrahydrofuran, dichloromethane, dimethylformamide, dimethyl sulphoxide, N-methylmorpholine and the like but any other solvent which does not have an adverse influence on the reaction may also be used.

The reaction is preferably carried out in the presence of an acid or a base. Examples of acids include inorganic acids (e.g., hydrochloric acid, sulphuric acid, hydrobromic acid, etc.), organic acids (e.g., formic acid, acetic acid, trifluoroacetic acid, propionic acid, benzene-sulphonic acid, p-toluene-sulphonic acid, etc.), and acidic ion exchange resins and the like. Examples of bases include those mentioned above in the description of Process 1.

A catalytic amount of the acid is more preferably used in the reaction of a compound (II) and the reactive equivalent, such as an olefinic heterocycle mentioned above, and a stoichiometrical or a molar excess of the base are usually used in the reaction of the compound (II) and other etherifying agent as mentioned above.

There is no limitation on the reaction temperature which is selected in accordance with the nature of the solvent and etherifying agent used.

(6) Process 6:
Acetalisation of compounds (II):
(Example 11)

In this process, compounds (VIII) can be prepared by reacting compounds (II) with a ketone or aldehyde of the general formula $R_d^1$=O, wherein $R_d^1$ is an alkylidene or aralkylidene radical.

Examples of the ketones and aldehydes include acetone acetaldehyde, benzaldehyde, salicylaldehyde and the like.

The reaction is conducted under substantially the same conditions (solvent, reaction temperature, etc.) and usually in the presence of catalytic amounts of an acid as given in the description of Process 5.

(7) Process 7:

Acylation of compounds (VIII):

(Example 29)

In this process, compounds (IX) can be prepared by reacting compounds (VIII) with acylating agents of the general formula $R_i$—OH, wherein $R_i$ is an acyl radical, or reactive derivatives thereof.

The acylating agent used in this process can be, for example, an aliphatic acid, an aromatic acid or a heterocyclic acid and, more particularly, an acylating agent of the general formula $R_i$—OH wherein $R_i$ is an acyl radical, examples of which include those given in the explanation of acyl above.

The reactive derivatives include acid halides, activated amides, activated esters, acid azides, symmetrical acid anhydrides, asymmetrical acid anhydrides with other acids, including alkyl-sulphonic acids, alkyl-phosphoric acids, etc. and the like.

The reaction is usually carried out in a conventional solvent, examples of which include water, acetone, dioxan, acetonitrile, chloroform, ethylene chloride, tetrahydrofuran, ethyl acetate, diethyl ether, pyridine, N,N-dimethylacetamide, dimethyl-sulphoxide, N,N-dimethylformamide, N-methylpyrrolidone, diglyme, triglyme, hexamethylphosphoramide and the like but any other solvent which does not have an adverse influence on the reaction may also be used.

The present reaction can also be carried out in the presence of a base, such as one of those given in the description of Process 1.

In the reaction, when a free acid or a salt thereof is employed as acylating agent, the reaction is preferably carried out in the presence of a condensation agent such as is conventionally used in acylation.

The reaction temperature is not limited but is usually carried out with cooling or at ambient temperature.

(8) Process 8:

Oxidative epoxidation of compounds (X):

(Examples 51–53)

In this process, compounds (XI) can be prepared by oxidising compounds (X) with oxidising agents.

Oxidation in this reaction is carried out in conventional manner with a conventional oxidising agent which can be used to oxidise an ethylenic double bond to the corresponding epoxide. Examples of oxidising agents include inorganic peracid or the salt thereof (e.g., periodic acid, persulphuric acid and the sodium and potassium salts thereof), organic peroxides and salts thereof (e.g., perbenzoic acid, m-chloroperbenzoic acid, m-bromoperbenzoic acid, performic acid, chloroperacetic acid, peracetic acid, trifluoroperaetic acid, monoperphthalic acid, monoperisophthalic acid, monoperterephthalic acid, methyl hydroperoxide, ethyl hydroperoxide, tert.-butyl hydroperoxide, etc., or the sodium or potassium salts thereof), hydrogen peroxide, a mixture of hydrogen peroxide and an acid corresponding to the above peracid and the like.

The reaction is usually carried out in a solvent, examples of which include water, methanol, ethanol, acetone, methylene chloride, ethylene chloride, formic acid, acetic acid, ethyl acetate, chloroform, diethyl ether, dioxan, tetrahydrofuran, benzene, toluene, hexane and the like. Hydrophilic solvents may be used in admixture with water.

When using hydrogen peroxide or a mixture of hydrogen peroxide and an acid as the oxidising agent, the reaction is preferably carried out in the presence of a compound of a metal of Group $V_b$ or $VI_b$ of the Mendeleeff Periodic Table, for example, tungstic acid, molybdic acid, vanadic acid, etc. or an alkali metal salt thereof (e.g., a sodium or potassium salt, etc.) or an alkaline earth metal salt thereof (e.g., calcium or magnesium salt, etc.) or ammonium salt thereof.

There is no limitation to the reaction temperature, which is selected in accordance with the nature of the starting material (X), the oxidising agent and the solvent used.

(9) Process 9:

Oxidative epoxidation of compounds (VIII):

(Example 54)

In this process, compounds (XII) can be prepared by oxidising compounds (VIII) with oxidising agents.

Examples of oxidising agents include those given in the description of Process 8.

The reaction is carried out using substantially the same oxidising agents and under substantially the same conditions (solvent, reaction temperature, etc.) as those given in the description of the reaction of Process 8.

(10) Process 10:

Cleavage of the epoxide ring of compounds (XI) with nucleophiles:

(Examples 14, 16–28)

In this process, compounds (XIII) can be prepared by reacting compounds (XI) with nucleophiles.

Examples of nucleophiles include those given in the description of the reaction of Process 3.

The reaction is carried out under substantially the same conditions (solvent, reaction temperature, etc.) as those used for the reaction of Process 3.

Under such reaction conditions, compounds (XIII) in which $R_f^1$ is a hydroxyl group, are usually obtained. When the reaction is carried out especially under reductive conditions, compounds (XIII) in which $R_f^1$ is a hydrogen atom are usually obtained.

(11) Process 11:

Cleavage of the epoxide ring of compounds (XII) with nucleophiles:

(Example 15)

In this process, compounds (XIV) can be prepared by reacting compounds (XII) with nucleophiles.

Examples of nucleophiles include those given in the description of the reaction of Process 3.

The reaction is carried out under substantially the same conditions (solvent, reaction temperature, etc.) as those given in the description of the reaction of Process 10, i.e. when the reaction is carried out under nonreductive conditions, compounds (XIV) are usually obtained in which $R_f^2$ is a hydroxyl group and when carried out under reductive conditions, compounds (XIV) in which $R_f^2$ is a hydrogen atom are usually obtained.

(12) Process 12:

Elimination of protective groups on hydroxyl groups of compounds (XV):

(Examples 47–48)

In this process, compounds (XVI) can be prepared by eliminating the protective group on hydroxyl groups of compounds (XV).

The elimination of the protective groups on hydroxyl groups of compounds (XV) can be carried out in conventional manner, such as acid hydrolysis. Examples of acids include inorganic acids (e.g. hydrochloric acid, sulphuric acid, hydrobromic acid, etc.), organic acids (e.g., formic acid, acetic acid, trifluoroacetic acid, propionic acid, benzene-sulphonic acid, p-toluene-sulphonic acid, etc.) and acidic ion exchange resins and the like.

The reaction can be carried out in a hydrophilic solvent, such as an alcohol (e.g., methanol, ethanol, etc.), in water or in a mixture thereof.

There is no limitation to the reaction temperature, the reaction usually being carried out with cooling or at ambient temperature or at a somewhat elevated temperature.

(13) Process 13:
Halogenation of compounds (X):
(Examples 49-50)

In this process, compounds (XVIII) can be prepared by reacting compounds (X) with halogenating agents.

Examples of halogenating agents include halogens (e.g., chlorine, bromine, etc.) and the like.

The reaction is usually carried out in a solvent, examples of which include conventional solvents which do not have an adverse influence on the reaction, for example, water, acetic acid, methylene chloride, carbon tetrachloride, dioxan and the like.

There is no limitation to the reaction temperature, which is selected in accordance with the nature of the starting material (X), the halogenating agent and the solvent used.

(14) Process 14:
Alkylation of compounds (XIX):
(Examples 30-46)

In this process, compounds (XX) can be prepared by reacting compounds (XIX) with alkylating agents of the general formula A—$Y_2$, wherein A is an aliphatic hydrocarbon radical and $Y_2$ is an acid residue.

Examples of aliphatic hydrocarbon radicals in the definition for A include those given in the description of $R_b^2$, $R_c^4$, $R_{II}^2$, $R_{III}^2$ and $R_{IV}^4$.

Examples of acid residues in the definition for $Y_2$ include acid residues of inorganic acids (e.g. hydrochloric acid, hydrobromic acid, hydriodic acid, sulphuric acid, alkyl sulphates, etc.), organic acids (e.g. methanesulphonic acid, benzene-sulphonic acid, toluene-sulphonic acid, etc.) and organic carbamic acids (e.g., dimethylcarbamic acid, diethylcarbamic acid, etc.).

The reaction is usually carried out in a solvent, examples of which include conventional solvents which do not have an adverse influence on the reaction, for example, acetone, methanol, ethanol, benzene, toluene, xylene, dioxan, dichloromethane, dimethylformamide, dimethyl sulphoxide and the like.

The reaction is preferably carried out in the presence of a base, such as an inorganic or organic base, examples of which include those given in the description of Process 1.

This reaction gives compounds (XX) in which at least one of $R_b^2$, $R_c^4$, $R_{II}^2$, $R_{III}^2$ and $R_{IV}^4$ is an aliphatic hydrocarbon radical. In this reaction, more than one of the aliphatic hydrocarbon radicals can be introduced optionally into the compounds (XX) as $R_b^2$, $R_c^4$, $R_{II}^2$, $R_{III}^2$ and $R_{IV}^4$, respectively, depending upon the amount of alkylating agent used and the reaction conditions; for example, when potassium carbonate is used as base, an aliphatic hydrocarbon radical is introduced mainly into the substituents $R_{II}^2$ and (or) $R_{III}^2$ of the compounds (XX).

(15) Process 15:
N-Alkylation of the compound (XXI):
(Example 55)

In this process, compounds (XXII) can be prepared by reacting compounds (XXI) with alkylating agents.

Examples of alkylating agents include diazoalkanes (e.g., diazomethane, diazoethane, etc.), dialkyl sulphates (e.g., dimethyl sulphate, diethyl sulphate, dipropyl sulphate, etc.), alkyl halides (e.g., methyl iodide, ethyl iodide, propyl iodide, etc.) and the like.

The reaction is usually carried out in a conventional solvent which does not have an adverse influence on the reaction, for example, water, acetone, methanol, ethanol, benzene, toluene, xylene, dioxan, dichloromethane, N,N-dimethylformamide, dimethyl sulphoxide or the like.

The reaction is preferably carried out in the presence of a base, examples of which include those given in the description of the Process 1.

There is no limitation to the reaction temperature but the reaction is usually carried out at ambient temperature.

The object compound of the present invention, bicyclomycin derivative (I) possesses antimicrobial activity against pathogenic microorganism and is useful as an antimicrobial agent for treatment of infectious disease in human and animals. And, it is to be noted that the object compound (I) is low in its toxicity.

Further, it is to be understand that the object compound (I) of the present invention is also useful as intermediates for preparing pharmaceutical compounds having antimicrobial activity.

The object compound (I) of the present invention can be administered by the conventional method, by the conventional unit dosages or with the conventional carriers for treatment of disease caused by pathogenic microorganisms.

Thus, the object compound (I) of the present invention can be used in the form of pharmaceutical preparations, for example, in solid, semisolid or liquid form, which contain the object compound (I) of the present invention, as an active ingredient, in admixture with a pharmaceutical organic or inorganic carrier or excipient suitable for external or parenteral applications. The active ingredient may be compounded, for example, with the usual carriers for tablets, peletts, capsules, suppositories, solutions, emulsions, aqueous suspensions and other form suitable for use. The carriers which can be used are glucose, lactose, gum acacia, gelatin, mannitol, starch paste, magnesium trisilicate, talc, corn starch, keratin, colloidal silica, potato starch, urea and other carrier suitable for use in manufacturing preparations, in solid, semisolid or liquid form, and in addition auxiliary, stabilizing, thickening and coloring agents and perfumes. The compositions of the present invention can also contain preservative or bacteriostatic agents therby keeping the active ingredient in the desired preparations stable in activity. The object compound (I) of the present invention is included in the compositions of the present invention in an amount sufficient to produce the desired therapeutic effect upon the bacterially infected process or condition. While the dosage or therapeutically effective quantity of the compound very from and also depend upon the age and condition of each individual patient being treated, a daily dose of about 0.5–5 g., preferably 1–2 g/day of the active ingredient is generally given for treating diseases infected by pathogenic microorganism.

Protecting Effect in Experimental Mice Infections:

For a reference's sake, with regard to antimicrobial activity of the typical compound which falls within the category of the compounds of the formula (I) of the present invention, there are illustrated in vivo tests in which active ingredient are the following compounds.

TEST COMPOUND

Compound 1: 2',3'-O,O-isopropylidenebicyclomycin
Compound 2: 5,11-dibromo-5,11-dihydrobicyclomycin

TEST METHOD

The test compound against in vivo against the species *Escherichia coli* was tested using female albino mice weighing 8 g–24 g.

The mice were infected by intraperitoneal route with standardized suitable diluted bacterial suspensions of E. coli strain 1075 and then treated subcutaneously with the test compound.

The $ED_{50}$ (mg/kg) was determined from the numbers of mice surviving on the 5th day after infection. The highest dosage tested was usually 300 mg/kg.

The results are given in the following.

| Result | $ED_{50}$ (mg/kg) |
|---|---|
| Compound 1: | 65 |
| Compound 2: | 60 |

The following Examples are given for the purpose of illustrating the present invention:

EXAMPLE 1

456 mg. 3'-p-toluene-sulphonylbicyclomycin were added, with cooling and stirring, to a solution obtained, by dissolving 94 mg. solution ethanethiolate in 10 ml. acetone. The solution was left to stand for 2 days and then filtered. The filtrate was washed with acetone, whereafter the filtrate and the washings were combined. The solvent was distilled off. The residue obtained was extracted with hot acetone and the extract was concentrated to give 360 mg. of an oily substance. This oily substance was crystallised from hot acetone to give 50 mg. of colourless prisms of 2',3'-anhydrobicyclomycin; m.p. 192°–195° C.

Elementary analysis for $C_{12}H_{16}N_2O_6$: calculated: C 50.70%; H 5.67%; N 9.86%. found: 51.00%; 5.73%; 9.80%.

In substantially the same manner as described in the above Example 1, there were obtained the compounds illustrated in the following Examples 2 and 3:

EXAMPLE 2

Starting material:
 4.56 g. 3'-p-toluene-sulphonylbicyclomycin
Base:
 1.10 g. triethylamine
Solvent for the reaction:
 20 ml. methanol
Compound obtained:
 1.92 g. 2',3'-anhydrobicyclomycin; m.p. 190°–194° C.

EXAMPLE 3

Starting material:
 450 mg. 3'-p-toluene-sulphonylbicyclomycin
Base:
 4 ml. N,N-dimethylaniline
Solvent for the reaction:
 4 ml. methanol
Compound obtained:
 30 mg. 2',3'-anhydrobicyclomycin.

The compound obtained was identified by comparing the infra-red absorption spectrum and thin layer chromatograph with those of the compound obtained in Example 1.

EXAMPLE 4

220 mg. 2',3'-Anhydrobicyclomycin were dissolved in 220 ml. methanol and one drop of triethylamine was added to the solution. Gaseous hydrogen sulphide was passed into the solution in water-bath at 22°–23° C. for 3 hours, while stirring. After further stirring the reaction mixture for 2 hours, aeration was carried out to remove the greater part of the hydrogen sulphide. The reaction mixture was concentrated to dryness. The residue was dissolved in a small amount of methanol and to the methanolic solution were added 15 ml. ethyl acetate, whereafter the precipitate formed was separated by filtration. The precipitate was washed with ethyl acetate and dried to give 160 mg. of a powder. The filtrate obtained as mentioned above and the washings as mentioned above were combined and concentrated under reduced pressure. The residue thus obtained was treated with 15 ml. ethyl acetate to give a powder. Both the powders obtained were combined and crystallised from a mixture of ethanol and ethyl acetate (1:4). The crystals were washed with carbon disulphide and then recrystallised from a mixture of ethanol and ethyl acetate (1:4) to give 45 mg. of colourless crystals of 3'-dehydroxy-3'-mercaptobicyclomycin; m.p. 168°–170° C. (dec.).

NMR absorption spectrum Solvent: pyridine-$d_5$ Internal standard: tetramethylsilane

| $\delta$(ppm) | |
|---|---|
| 1.91 | (3H, singlet) |
| ca. 2.5–3.0 | (2H, multiplet) |
| 3.87 | (2H, singlet) |
| ca. 3.9–4.3 | (2H, multiplet) |
| 4.92 | (1H, singlet) |
| 5.16 | (1H, broad singlet) |
| 6.02 | (1H, broad singlet) |

EXAMPLE 5

1.14 g. 2',3'-Anhydrobicyclomycin was dissolved in methanol and to the solution obtained was added 0.46 g. thioacetic acid. Two drops of triethylamine were added to the solution, whereafter the solution was stirred for 4 hours at ambient temperature. The reaction mixture was concentrated under reduced pressure to give a residue which was dissolved in a small amount of ethanol. Diethyl ether was added to the solution which was then stirred for 2 hours to give a precipitate. The precipitate was dried to give 1.07 g. of a powder which was crystallised from 5 ml. acetone to give 490 mg. of crystals. The mother liquor was concentrated to give 350 mg. of crystals. These crystals were combined and recrystallised from acetone to give 570 mg. of colourless crystals of 3'-dehydroxy-3'-acetylthiobicyclomycin.

NMR absorption spectrum Solvent: dimethyl sulphoxide-$d_6$ Internal standard: tetramethylsilane

| δ(ppm) | |
| --- | --- |
| 1.15 | (3H, singlet) |
| ca. 2.3–2.7 | (2H, multiplet) |
| 2.32 | (3H, singlet) |
| ca. 2.99 | (1H, doublet, $J_{AB} \approx 11$ Hz) |
| ca. 3.39 | (1H, doublet, $J_{AB} \approx 11$ Hz) |
| ca. 3.6–4.0 | (2H, multiplet) |
| ca. 3.86 | (1H, doublet, $J = 6.5$ Hz) |
| 5.08 | (1H, broad singlet) |
| 5.40 | (1H, broad singlet) |
| 5.47 | (1H, doublet) |
| 5.80 | (1H, singlet) |
| 6.79 | (1H, singlet) |
| 8.66 | (1H, singlet) |
| 8.73 | (1H, singlet) |

EXAMPLE 6

130 mg. 2',3'-Anhydrobicyclomycin were added to 8 ml. methanol and then the mixture was heated, whereafter 60 mg. thiophenol and a small amount of triethylamine were added to the solution. The solution was stirred for 80 minutes at ambient temperature. The reaction mixture was concentrated under reduced pressure to give a colourless oily substance. 3 ml. ethyl acetate were added to the oily substance and then the mixture was heated, whereafter the mixture was cooled to give colourless crystals. The crystals were recrystallised three times from ethyl acetate to give 20 mg. colourless silky crystals of 3'-dehydroxy-3'-phenylthiobicyclomycin; m.p. 168°–169° C.

Elemental analysis for $C_{18}H_{22}N_2SO_6$: calculated: C 54.81%; H 5.62%; N 7.10%; S 8.13%. found: 54.52%; 5.57%; 6.98%; 8.30%.

EXAMPLE 7

140 mg. 2',3'-Anhydrobicyclomycin were dissolved in 6 ml. methanol and then 90 mg. aniline were added to the solution, whereafter the solution was refluxed for 4 hours. The reaction mixture was left to stand overnight and then the methanol was distilled off. The residue thus obtained was dissolved in ethyl acetate and then the solution was washed with water and concentrated under reduced pressure to give 130 mg. of a powder. The powder was recrystallised twice from ethyl acetate to give 60 mg. of colourless short needles of 3'-dehydroxy-3'-anilinobicyclomycin; m.p. 157°–159° C.

Elementary analysis for $C_{18}H_{23}N_3O_6$ calculated: C 57.28%; H 6.14%; N 11.14%. found: 57.22%; 6.13%; 11.13%.

EXAMPLE 8

15.1 g. Bicyclomycin were dissolved in 60 ml. pyridine and then 9.5 g. p-toluene-sulphonyl chloride were added dropwise, with stirring, to the solution in an ice-sodium chloride bath, keeping the temperature at −15° C. The mixture was further stirred for 2 hours at the same temperature and then the reaction mixture was poured into a mixture of 78 ml. hydrochloric acid and 350 ml. ice-water. The oily substance obtained was extracted three times with ethyl acetate. The ethyl acetate extracts were combined and successively washed with ice-water, cold aqueous sodium bicarbonate solution and ice-water. The ethyl acetate layer was dried over anhydrous magnesium sulphate and then the ethyl acetate was distilled off. The residue obtained (11.4 g.) was recrystallised from ethyl acetate to give 9.17 g. of colourless needles of 3'-p-toluene-sulphonylbicyclomycin; m.p. 101°–103° C.

Elementary analysis for $C_{19}H_{24}N_2SO_9$: calculated: C 49.99%; H 5.30%; N 6.14%; S 7.02%; found: 49.84%; 5.20%; 5.94%; 7.04%.

EXAMPLE 9

910 mg. 3'-p-Toluene-sulphonylbicyclomycin were added to a solution prepared by dissolving 200 mg. potassium thiocyanate into 10 ml. anhydrous acetone, whereafter the solution was gently refluxed for 4.5 hours to give crystals. The crystals were filtered off and the filtrate was evaporated to dryness. The residue obtained was recrystallised twice from methanol to give 100 mg. of colourless prisms of 8,10-diaza-6-hydroxy-5-methylene-1-(2-imino-5-hydroxy-5-methyl-1,3-oxa-thiane-6-yl)-2-oxabicyclo[4,2,2]decane-7,9-dione.

Elementary analysis for $C_{13}H_{17}N_3SO_6$: calculated: C 45.47%; H 4.99%; N 12.24%; S 9.34%. found: 45.23%; 4.90%; 12.09%; 9.57%.

NMR absorption spectrum Solvent: dimethyl sulphoxide-$d_6$ Internal Standard: tetramethylsilane

| δ(ppm) | |
| --- | --- |
| 1.29 | (3H, singlet) |
| ca. 2.28–2.65 | (2H, multiplet) |
| ca. 2.90–3.60 | (2H, multiplet) |
| ca. 3.32 | (1H, doublet, $J_{AB} \approx 9.0$ Hz) |
| ca. 3.64 | (1H, doublet, $J_{AB} \approx 9.0$ Hz) |
| 4.78 | (1H, singlet) |
| 5.52 | (1H, doublet, $J \approx 2$ Hz) |
| 5.74 | (1H, singlet) |
| 6.45 | (1H, singlet) |
| 7.79 | (1H, singlet) |
| 9.07 | (1H, singlet) |
| 10.56 | (1H, singlet) |

EXAMPLE 10

18.12 g. Bicyclomycin were dissolved in 50 ml. pyridine and 16.8 g. triphenyl-methyl chloride were added to the solution, which was then left to stand for 24 hours at ambient temperature. Thereafter, water was added to the reaction mixture and then the pyridine was distilled off under reduced pressure. Ethyl acetate and water were added to the residue obtained, whereafter the mixture was stirred. The ethyl acetate layer thus obtained was washed three times with water and then dried over anhydrous magnesium sulphate, whereafter the layer was concentrated under reduced pressure. The residue thus obtained was recrystallised from a mixture of benzene and ether to give 15 g. of colourless crystals of 3'-O-triphenylmethylbicyclomycin; m.p. 155°–157° C.

EXAMPLE 11

5 g. Finely powdered bicyclomycin were suspended in 150 ml. acetone, followed by cooling to below 0° C. 4 drops of concentrated sulphuric acid were added to the suspension, which was stirred for 30 minutes at the same temperature and further stirred for 5 hours at 10°–12° C. The reaction mixture was cooled with ice-water and 15 drops of aqueous sodium bicarbonate solution were added to the reaction mixture. The solution was filtered and the filtrate was concentrated under reduced pressure. Ethanol was added to the residue obtained to give a precipitate which was washed with a small amount of ethanol and then dried to give 3.61 g.

colourless prisms of 2',3'-O,O-isopropylidenebicyclomycin; m.p. 201°–204° C.

Elementary analysis for $C_{15}H_{22}N_2O_7$: calculated: C 52.62%; H 6.48%; N 8.18%. found: 52.23%; 6.51%; 8.02%.

EXAMPLE 12

6.1 g. Bicyclomycin were dissolved in 18 ml. dimethylformamide and to the solution were added 5.5 g. 3,4-dihydro-2H-pyran and 0.1 g. p-toluene-sulphonic acid monohydrate. The solution was stirred for 4 days at ambient temperature. 40 ml. ice-water were added to the reaction mixture, followed by extraction three times with diethyl ether. The ethereal layer was washed with water and dried over anhydrous magnesium sulphate, whereafter the ethereal layer was concentrated under reduced pressure to give 2 g. of a residue. To the residue there were added 5 ml. diisopropyl ether to give 0.6 g. of a crystalline powder. The powder was recrystallised from diisopropyl ether to give 0.5 g. of colourless crystals of 1',3'-O,O-di(tetrahydropyran-2-yl)-bicyclomycin; m.p. 183°–185° C.

Elementary analysis for $C_{22}H_{34}N_2O_9$: calculated: C 56.16%; H 7.28%; N 5.95%. found: 56.25%; 7.48%; 5.82%.

EXAMPLE 13

To 120 ml. 3,4-dihydro-2H-pyran was added 0.5 g. p-toluene-sulphonic acid, with cooling and stirring, and then 30 g. of finely powdered bicyclomycin were added thereto. The solution was stirred for 6 days at 15°–18° C. and then 150 ml. diethyl ether were added thereto. The solution was filtered and the filtrate was cooled and washed with aqueous sodium bicarbonate solution. The filtrate was further washed five times with ice-water and then dried over anhydrous magnesium sulphate. The solution was concentrated under reduced pressure to give 84 g. of an oily substance. 200 ml. n-Hexane were added to the oily substance. The mixture was warmed and then stirred to give a precipitate, which was left to stand for 1 hour at $-15°$ C. The precipitate was filtered off and dried under reduced pressure to give 36 g. of a pale yellowish powder of 6,1',3'-O,O,O-tri(tetrahydropyran-2-yl)bicyclomycin.

NMR absorption spectrum Solvent: dimethyl sulphoxide-$d_6$ Internal standard: tetramethylsilane

| $\delta$(ppm) | |
|---|---|
| ca. 1.3–2.2 | (21H, multiplet) |
| ca. 2.5–2.7 | (2H, multiplet) |
| ca. 3.2–4.3 | (10H, multiplet) |
| 4.45 | (1H, singlet) |
| ca. 4.5–4.9 | (3H, multiplet) |
| 5.13 | (1H, broad singlet) |
| 5.63 | (1H, broad singlet) |

EXAMPLE 14

1.20 g. 3'-O-Benzoyl-5,11-epoxybicyclomycin was dissolved in 50 ml. 99% ethanol and 0.25 g. diethylamine was added thereto, whereafter the reaction mixture was stirred at ambient temperature for 46 hours. The precipitated crystals in the reaction mixture were filtered off and then washed with a small amount of ethanol to give 0.95 g. of colourless prisms of 3'-O-benzoyl-11-diethylamino-5-hydroxy-5,11-dihydrobicyclomycin; m.p. 188° to 189° C. (dec.).

Elemental analysis for $C_{23}H_{33}N_3O_9$: calculated: C 55.75%; H 6.71%; N 8.48%. found: 55.65%; 6.69%; 8.38%.

EXAMPLE 15

1.08 g. 5,11-Epoxy-2',3'-O,O-isopropylidenebicyclomycin and 0.03 g. triethylamine were dissolved in 16 ml. methanol. 0.40 g. ethyl thioglycolate was added to the solution under an atmosphere of nitrogen, whereafter the reaction mixture was heated at 50° to 52° C. for 8.5 hours and then left to stand at ambient temperature overnight. The reaction mixture was evaporated to dryness under reduced pressure to give 1.2 g. of yellow-brown residue which was dissolved in ethyl acetate. The solution was treated with activated charcoal and evaporated to dryness to give a residue. The residue was recrystallised repeatedly from acetonitrile to give 0.4 g. of a colourless powder of 11-ethoxycarbonyl-methylthio-5-hydroxy-2',3'-O,O-isopropylidene-5,11-dihydrobicyclomycin; m.p. 156°–159° C.

EXAMPLE 16

2.11 g. 3'-O-Benzoyl-5,11-epoxybicyclomycin were dissolved in 60 ml. 99% ethanol. 0.90 g. ethyl thioglycolate and 0.10 g. triethylamine were added thereto, under an atmosphere of nitrogen, whereafter the reaction mixture was stirred at 50° C. for 25 hours. The reaction mixture was evaporated to dryness to give a residue, which was dissolved in ethyl acetate. The solution was washed with water and then dried, whereafter the solvent was distilled off from the solution under reduced pressure to give 1.9 g. of a powdery residue. The residue was dissolved in 10 ml. chloroform and diethyl ether was added thereto a little at a time, with stirring, until no further precipitation was produced. The precipitate was filtered off and then diethyl ether was added to the filtrate a little at a time. The precipitated powder was filtered off and this powder and the previously obtained powder were combined to give 1.54 g. of a colourless powder of 3'-O-benzoyl-5-ethoxycarbonyl-methylthio-5-hydroxy-5,11-dihydrobicyclomycin; m.p. 115° C. (dec.).

Elemental analysis for $C_{23}H_{30}N_2O_{11}S$: calculated: C 50.91%; H 5.57%; N 5.16%; S 5.91%. found: 51.23%; 5.52%; 4.96%; 6.10%.

EXAMPLE 17

1.9 g. 3'-O-Butyryl-5,11-epoxybicyclomycin was dissolved in 50 ml. 99% ethanol and 0.9 g. ethyl thioglycolate and 0.1 g. triethylamine were added thereto. The reaction mixture was treated in substantially the same way as in Example 16 to give 1.46 g. of a colourless powder of 3'-O-butyryl-11-ethoxycarbonyl-methylthio-5-hydroxy-5,11-dihydrobicyclomycin.

NMR absorption spectrum: (internal standard: tetramethylsilane)

| $\delta$ppm (pyridine-$d_6$) | |
|---|---|
| 0.87 | (3H, t, J=7.3 Hz) |
| 1.12 | (3H, t, J=7.0 Hz) |
| 1.63 | (2H, hex, J=7.3 Hz) |
| 1.75 | (3H, s) |
| 2.30 | (2H, t, J=7.3 Hz) |
| ca. 2.4–2.8 | (2H, m) |
| ca. 3.38 | (1H, d, $J_{AB} \approx$ 14 Hz) |
| 3.55 | (2H, s) |
| ca. 3.9–4.4 | (2H, m) |
| 4.08 | (2H, q, J=7.0 Hz) |
| ca. 4.11 | (1H, d, $J_{AB} \approx$ 14 Hz) |

| δppm (oyridine-d6) | |
|---|---|
| ca. 4.61 | (1H, d, $J_{AB} \approx$ 12 Hz) |
| 4.77 | 1H, s) |
| ca. 4.84 | (1H, d, $J_{AB} \approx$ 12 Hz) |

EXAMPLE 18

2.3 g. 3'-O-Butyryl-5,11-epoxybicyclomycin, 0.90 g. thioacetate acid and 0.04 g. triethylamine were dissolved in 20 ml. ethanol, whereafter the reaction mixture was stirred at 35° to 40° C. for 26 hours. The ethanol was distilled off from the reaction mixture under reduced pressure to give a residue which was dissolved in ethyl acetate. The solution was washed with an aqueous sodium bicarbonate solution and dried over anhydrous magnesium sulphate. The solvent was distilled off from the solution under reduced pressure to give 2.74 g. of a residue which was dissolved in 14 ml. chloroform. Diethyl ether was added to the solution a little at a time until no further precipitate was produced. The precipitate was filtered off and washed with diethyl ether to give 1.8 g. of a powder. The powder was subjected to reprecipitation with 5 ml. chloroform and 25–30 ml. of a mixture of ether and petroleum ether to give 1.55 g. of a colourless powder of 3'-O-butyryl-5-hydroxy-11-acetylthio-5,11-dihydrobicyclomycin; m.p. 100° to 115° C.

EXAMPLE 19

0.42 g. 3'-O-Benzoyl-5,11-epoxybicyclomycin was dissolved in 14 ml. 99% ethanol and 0.21 g. glycin ethyl ester hydrochloride and 0.15 g. triethylamine were added thereto, whereafter the reaction mixture was stirred at ambient temperature for 10 hours. The reaction mixture was evaporated to dryness under reduced pressure to give a residue, which was dissolved in ethyl acetate. The solution was washed with water and dried, whereafter the solvent was distilled off from the solution under reduced pressure to give 0.42 g. of a residue. The residue was treated with a mixture of ethyl acetate and ether (volume ratio 2:15) and the 0.38 g. of powder obtained was treated with 5 ml. benzene to give 0.35 g. of a colourless powder of 3'-O-benzoyl-11-ethoxycarbonylmethylamino-5-hydroxy-5,11-dihydrobicyclomycin which melted at 115° to 120° C. and decomposed at about 150° C.

Elemental analysis for $C_{23}H_{31}N_3O_{11}$ calculated: C 52.57%; H 5.95%. found: 52.64%; 5.91%.

EXAMPLE 20

0.42 g. 3'-O-Benzoyl-5,11-epoxybicyclomycin was dissolved in 14 ml. 99% ethanol and 0.13 g. 2-mercapto-5-methyl-1,3,4-thiadiazole and 0.05 g. triethylamine were added to the solution, whereafter the reaction mixture was stirred at ambient temperature for 26.5 hours. The reaction mixture was then evaporated to dryness under reduced pressure to give a residue which was dissolved in ethyl acetate. The solution obtained was washed with water and then dried and then concentrated, whereafter it was left to stand, a powdery precipitate being obtained. The powder was filtered off, washed with a small amount of ethyl acetate and dried to give 0.43 g. of a colourless powder of 3'-O-benzoyl-5-hydroxy-11-(5-methyl-1,3,4-thiadiazol-2-ylthio)-5,11-dihydrobicyclomycin which melted at 134° to 145° C. and decomposed at 160° to 170° C.

Elemental analysis for $C_{22}H_{26}N_4O_9S_2$: calculated: C 47.64%; H 4.73%; N 10.10%. found: 47.57%; 4.62%; 9.83%.

EXAMPLE 21

1.06 g. 3'-O-Benzoyl-5,11-epoxybicyclomycin was dissolved in 50 ml. 99% ethanol and 3 drops of triethylamine were added to the solution. Hydrogen sulphide was passed into the solution for 3.3 hours and then the reaction mixture was left to stand overnight. The reaction mixture was evaporated to dryness under reduced pressure and the residue obtained was dissolved in ethyl acetate. The solution was washed with water and dried, whereafter the solvent was distilled off from the solution under reduced pressure to give 1.3 g. of a residue. The residue was dissolved in 3 ml. butyl acetate, with warming, and diisopropyl ether was added to the solution a little at a time until no further precipitate was produced. The powdery precipitate was filtered off and the reprecipitation was repeated to give 1.0 g. of a colourless powder of 3'-O-benzoyl-5-hydroxy-11-mercapto-5,11-dihydrobicyclomycin which melted at 132° ro 140° C. and decomposed at 155° to 160° C.

Elemental analysis for $C_{19}H_{24}N_2O_9S$: calculated: C 49.99%; H 5.30%; N 6.14%; S 7.02%. found: 49.84%; 5.10%; 6.28%; 7.11%.

EXAMPLE 22

2.1 g. 3'-O-Benzoyl-5,11-epoxybicyclomycin, 0.75 g. thioacetic acid and 0.05 g. triethylamine were dissolved in 40 ml. 99% ethanol and the reaction mixture was stirred at 35° to 40° C. for 26 hours. The reaction mixture was evaporated to dryness and the residue obtained was dissolved in ethyl acetate. The solution was washed with a saturated aqueous sodium bicarbonate solution and then with water and dried over anhydrous magnesium sulphate. The solvent was distilled off from the solution under reduced pressure to give 2.2 g. of a colourless oily residue which was dissolved in 10 ml. chloroform. About 30 ml. diethyl ether were added to the solution a little at a time, while stirring, to give a powdery precipitate which was filtered off and washed with diethyl ether. This operation was repeated twice to give 1.70 g. of a colourless powder of 3'-O-benzoyl-5-hydroxy-11-acetylthio-5,11-dihydrobicyclomycin; m.p. 178° C. (dec.).

EXAMPLE 23

0.42 g. 3'-O-Benzoyl-5,11-epoxybicyclomycin and 0.15 g. aniline were dissolved in 20 ml. 99% ethanol, whereafter the reaction mixture was stirred at ambient temperature for 9 hours and then left to stand overnight. The solvent was distilled off from the reaction mixture under reduced pressure to give a residue which became powdery when diethyl ether was added thereto. The powder thus obtained was dissolved in a mixture of chloroform and carbon tetrachloride (volume ratio 5:95), with warming, and left to stand to cool to ambient temperature. 0.4 g. of a colourless powder of 11-anilino-3'-O-benzoyl-5-hydroxy-5,11-dihydrobicyclomycin was obtained; m.p. 135° to 145° C.

EXAMPLE 24

1.05 g. 3'-O-Benzoyl-5,11-epoxybicyclomycin was dissolved in 50 ml. 99% ethanol and 0.33 g. diethanolamine was added to the solution, whereafter the reaction mixture was stirred at ambient temperature for 43 hours. The solvent was distilled off from the reaction mixture under reduced pressure to give an oily residue which was subjected to column chromatography using silica gel. The column was eluted with acetone and the fractions containing the desired compound were collected and combined. The solvent was distilled off from the solution under reduced pressure to give 0.55 g. of colourless, oily 3'-O-benzoyl-11-N,N-bis-(2-hydroxyethyl)-amino-5-hydroxy-5,11-dihydrobicyclomycin which was converted into powder with diethyl ether.

NMR absorption spectrum: (internal standard: tetramethylsilane)

| δppm ((CD$_3$)$_2$SO): | |
|---|---|
| 1.35 | (3H, s) |
| ca. 1.60–1.85 | (2H, m) |
| ca. 2.4–2.9 | (6H, m) |
| ca. 3.3–3.6 | (4H, m) |
| ca. 3.5–3.8 | (2H, m) |
| 3.97 | (1H, s) |
| 4.37 | (2H, broad s) |

EXAMPLE 25

0.76 g. 3'-O-Butyryl-5,11-epoxybicyclomycin was dissolved in 7 ml. 99% ethanol and 0.22 g. diethylamine was added to the solution, whereafter the reaction mixture was stirred at ambient temperature for 24 hours. The ethanol was distilled off from the reaction mixture under reduced pressure and the residue obtained was recrystallised from a small amount of ethanol to give 0.6 g. of colourless prisms of 3'-O-butyryl-11-diethylamino-5-hydroxy-5,11-dihydrobicyclomycin; m.p. 148° to 150° C. (dec.).

Elemental analysis for C$_{20}$H$_{35}$N$_3$O$_9$: calculated: C 52.05%; H 7.64%; N 9.11%. found: 51.91%; 7.71%; 9.00%.

EXAMPLE 26

0.945 g. 3'-O-Butyryl-5,11-epoxybicyclomycin was dissolved in 8 ml. 99% ethanol and 0.30 g. aniline was added to the solution, whereafter the reaction mixture was stirred at ambient temperature for 48 hours. The solvent was distilled off from the reaction mixture under reduced pressure and the residue obtained was dissolved in ethyl acetate. The solution was washed with water and dried, whereafter the solvent was distilled off from the solution under reduced pressure. The residue thus obtained was crystallised from aqueous methanol to give 0.6 g. of crude crystals which were crystallised from aqueous methanol to give 0.45 g. of colourless flakes of 11-anilino-3'-O-butyryl-5-hydroxy-5,11-dihydrobicyclomycin; m.p. 135° C. (dec.).

Elemental analysis for C$_{22}$H$_{31}$N$_3$O$_9$: calculated: C 54.88%; H 6.49%; N 8.73%. found: 54.59%; 6.52%; 8.52%.

EXAMPLE 27

0.64 g. 5,11-Epoxybicyclomycin was dissolved in 6 ml. ethanol and 2 ml. acetic acid and 0.06 g. platinum dioxide catalyst were added to the solution, whereafter the reaction mixture was stirred at ambient temperature for 2 hours in an atmosphere of hydrogen. The catalyst was filtered off and washed with ethanol. The washings and the filtrate were combined. The solution was evaporated to dryness under reduced pressure and the residue obtained was converted into a powder with diethyl ether. The powder was subjected to column chromatography using silica gel. Elution was carried out with a mixture of chloroform and methanol (volume ratio 10:1), whereafter the fractions containing the desired compound were collected and combined. The solvent was distilled off from the solution under reduced pressure and the 0.20 g. of powder obtained was recrystallised from ethyl acetate to give 0.16 g. of colourless prisms of 11-acetoxy-5,11-dihydrobicyclomycin; m.p. 183° to 184° C. (dec.).

NMR absorption spectrum: (internal standard: tetramethylsilane)

| δppm (CD$_3$OD): | |
|---|---|
| 1.40 | (3H, s) |
| 2.16 | (3H, s) |
| ca. 2.0–2.3 | (2H, m) |
| ca. 3.60 | (1H, q, J$_{AB}$ ≈ 11.2 Hz) |
| ca. 3.80 | (1H, q, J$_{AB}$ ≈ 11.2 Hz) |
| ca. 3.9–4.3 | (2H, m) |
| 4.13 | (1H, s) |
| 4.39 | (2H, s) |

EXAMPLE 28

1.05 g. 3'-O-Benzoyl-5,11-epoxybicyclomycin was dissolved in 50 ml. 99% ethanol and 0.32 g. thiophenol and one drop of triethylamine were added thereto, whereafter the reaction mixture was left to stand at ambient temperature for 40 hours. The solvent was distilled off from the reaction mixture under reduced pressure to give a residue which was treated with 40 ml. n-hexane to give a pale yellowish powder. The powder was dissolved in a small amount of chloroform and n-hexane was added to the solution a little at a time, with stirring, until no further powder was produced. The powder was filtered off and dried under reduced pressure to give 1.2 g. of a colourless powder of 3'-O-benzoyl-5-hydroxy-11-phenylthio-5,11-dihydrobicyclomycin.

NMR absorption spectrum: (internal standard: tetramethylsilane)

| δppm ((CD$_3$)$_2$SO) | |
|---|---|
| 1.38 | (3H, s) |
| ca. 1.8–2.2 | (2H, m) |
| ca. 3.08 | (1H, d, J$_{AB}$ ≈ 13.5 Hz) |
| ca. 3.62 | (1H, d, J$_{AB}$ ≈ 13.5 Hz) |
| ca. 3.6–3.9 | (2H, m) |
| 4.03 | (1H, s) |
| 4.37 | (2H, s) |
| 7.24 | (5H, s) |
| ca. 7.40–7.65 | (3H, m) |
| ca. 7.80–8.05 | (2H, m) |

EXAMPLE 29

2.6 g. 2',3'-O,O-Isopropylidenebicyclomycin were dissolved in 6 ml. pyridine and 4.5 ml. acetic anhydride were added to the solution, whereafter the reaction mixture was stirred at 10° to 15° C. for 6 hours. The reaction mixture was poured into 80 ml. ice-water, while stirring, to give a precipitate which was subjected to filtration. The precipitate was washed and recrystallised from ethanol to give 2.6 g. of colourless crystals of 1',6-diacetyl-2',3'-O,O-isopropylidenebicyclomycin; m.p. 244° C. (dec.).

Elemental analysis for C$_{19}$H$_{26}$N$_2$O$_9$: calculated: C 53.51%; H 6.15%; N 6.57%. found: 53.36%; 6.31%; 6.42%.

EXAMPLE 30

4.0 g. 3'-O-Benzoylbicyclomycin were dissolved in 20 ml. N,N-dimethylformamide and 1.5 g. anhydrous potassium carbonate and 20 g. ethyl iodide were added to the solution, whereafter the reaction mixture was stirred at ambient temperature for 20 hours. The reaction mixture was poured into 50 ml. ice-water and the mixture was extracted twice with 50 ml. amounts of ethyl acetate. The extract was washed with water and dried over anhydrous magnesium sulphate. The solution was concentrated to give 3.6 g. of an oily material which was subjected to column chromatography using silica gel. Elution was carried out with chloroform and with a mixture of chloroform and methanol (volume ratio 100:1 and then 100:3). The fractions containing the desired compound were collected and combined. The solvent was distilled off from the solution under reduced pressure to give 1.5 g. of a residue. The residue was recrystallised from a mixture of 2 ml. ethyl acetate and 2 ml. diisopropyl ether to give 0.58 g. of needle-like crystals of N(8 or 10)-ethyl-3'-O-benzoylbicyclomycin; m.p. 170° to 171° C.

Elemental analysis for $C_{21}H_{26}N_2O_8$ calculated: C 58.06%; H 6.03%; N 6.45%. found: 57.98%; 6.01%; 6.33%.

EXAMPLE 31

6.1 g. 3'-O-Benzoylbicyclomycin were dissolved in 24 ml. N,N-dimethylformamide and 3.1 g. anhydrous potassium carbonate and 3.3 g. ethyl 2-bromoacetate were added to the solution, whereafter the reaction mixture was stirred at ambient temperature for 15 hours. The reaction mixture was poured into 70 ml. ice-water and the mixture was extracted three times with ethyl acetate. The extract was washed four times with water and dried over anhydrous magnesium sulphate. The solution was concentrated under reduced pressure to give 6.0 g. of an oily material which was dissolved in a mixture of 5 ml. ethyl acetate and 3 ml. diisopropyl ether. The solution was left to stand to precipitate crystals which were filtered off. The mother liquor thus obtained was used in the following Example 32. The 0.95 g. of crystals obtained were recrystallised from a mixture of 5 ml. ethyl acetate and 5 ml. diisopropyl ether to give 0.71 g. of colourless prisms of N(8 or 10)-ethoxycarbonylmethyl-3'-O-benzoylbicyclomycin; m.p. 180.5°–181.5° C. The mother liquor obtained from this recrystallisation was also used in the following Example 32.

Elemental analysis for $C_{23}H_{28}N_2O_{10}$: calculated: C 56.09%; H 5.73%; N 5.69%. found: 56.04%; 5.78%; 5.45%.

EXAMPLE 32

The mother liquors obtained in Example 31 above were combined and the solvent was distilled off under reduced pressure to give a residue which was subjected to column chromatography using 5 g. silica gel. Elution was carried out with chloroform and a mixture of chloroform and methanol (volume ratio 100:2). The fractions containing the desired compound were collected and combined. The solvent was distilled off from the solution under reduced pressure to give 0.76 g. powdery bis-(ethoxycarbonylmethyl)benzoyl-bicyclomycin.

NMR absorption spectrum: (internal standard: tetramethylsilane)

| $\delta$ppm ((CD$_3$)$_2$SO) | |
|---|---|
| 1.16 | (3H, t, J=7.0 Hz) |
| 1.18 | (3H, t, J=7.0 Hz) |
| 1.37 | (3H, s) |
| ca. 1.90–2.60 | (2H, m) |
| ca. 3.55–3.85 | (2H, m) |
| 3.89 | (2H, s) |
| 4.05 | (2H, q, J=7.0 Hz) |
| 4.08 | (1H, d, J=8.0 Hz) |
| 4.11 | (2H, q, J=7.0 Hz) |
| 4.29 | (4H, s) |
| 5.26 | (1H, broad s) |
| 5.52 | (1H, broad s) |
| 5.76 | (1H, d, J=8.0 Hz) |
| 6.05 | (1H, s) |
| ca. 7.25–7.40 | (3H, m) |
| ca. 7.85–8.10 | (2H, m) |
| 9.25 | (1H, s) |

EXAMPLE 33

6.09 g. 3'-O-Benzoylbicyclomycin were dissolved in 24 ml. N,N-dimethylformamide and 2.5 g. anhydrous potassium carbonate were added thereto. To the mixture was added 3.2 g. N,N-diethyl-2-bromoacetamide, while cooling with ice-water, and the reaction mixture was stirred at the same temperature for an hour and then at ambient temperature for 4 hours. The reaction mixture was poured into 50 ml. ice-water and the separated oily material was extracted three times with ethyl acetate. The extracts were combined and washed seven times with a saturated aqueous sodium chloride solution and then dried over anhydrous magnesium sulphate. The solvent was distilled off from the solution under reduced pressure to give 7.6 g. of residue, which was caused to crystallise by adding a small amount of ethyl acetate and diethyl ether thereto, 5.1 g. of crude crystals being obtained by filtration. The mother liquor was concentrated under reduced pressure and diethyl ether added to the concentrate to give 1.2 g. crude crystals. These crystals were combined and recrystallised from a mixture of ethyl acetate and diethyl ether to give 4.36 g. of colourless rhombic crystals of N(8 or 10)-diethylaminocarbonylmethyl-3'-O-benzoylbicyclomycin; m.p. 110° to 112° C.

Elemental analysis for $C_{25}H_{33}O_9N_2$ calculated: C 57.79%; H 6.40%; N 8.09%. found: 57.64%; 6.56%; 7.81%.

EXAMPLE 34

4.0 g. 3'-O-Benzoylbicyclomycin were dissolved in 12 ml. N,N-dimethylformamide and 1.7 g. anhydrous potassium carbonate and 2.2 g. phenacyl bromide were added thereto, whereafter the reaction mixture was stirred at ambient temperature for 2 hours. The reaction mixture was treated in substantially similar manner so that described in Example 33 to give 1.57 g. of colourless crystals of N-(8 or 10)-phenacyl-3'-O-benzoylbicyclomycin; m.p. 181°–182° C. (dec.).

Elemental analysis for $C_{27}H_{28}O_9N_2$ calculated: C 61.82%; H 5.38%; N 5.34%. found: 62.01%; 5.57%; 5.32%.

EXAMPLE 35

4.0 g. 3'-O-Benzoylbicyclomycin were dissolved in 12 ml. N,N-dimethylformamide and 1.7 g. anhydrous potassium carbonate added thereto. 1.5 g. Bromoacetone was added dropwise to the mixture over the course of 15 minutes, while cooling with ice-water and stirring, whereafter the reaction mixture was stirred at the same temperature for 3 hours. 30 ml. ice-water and 30 ml. of a saturated aqueous sodium chloride solution were poured into the reaction mixture and the mixture was extracted four times with 30 ml. amounts of ethyl acetate. These extracts were combined and washed three times with a 15% aqueous sodium chloride solution and three times with water, whereafter the solution was dried over anhydrous magnesium sulphate. The solvent was distilled off from the solution under reduced pressure to give 4.0 g. of an oily residue which was subjected to column chromatography, using silica gel. Elution was carried out with chloroform and a mixture of chloroform and ethanol (volume ratio 100:1) and the fractions containing the desired compound were collected. These fractions were combined and the solvent was distilled off from the solution under reduced pressure to give 1.8 g. of a powder. The powder was dissolved in 3 ml. ethyl acetate and 30 ml. diisopropyl ether were added thereto, while stirring. The precipitated crystals were filtered off and dried in a vacuum at 75° C. for 10 hours to give 1.73 g. of a colourless powder of acetonylated 3'-O-benzoylbicyclomycin.

NMR absorption spectrum: (internal standard; tetramethylsilane)

| $\delta$ppm (($CD_3$)$_2$SO) | |
|---|---|
| 1.39 | (3H, s) |
| 2.08 | (3H, s) |
| ca. 2.2–2.6 | (2H, m) |
| ca. 3.6–3.9 | (2H, m) |
| ca. 3.62 | (1H, d, $J_{AB} \approx 13.5$ Hz) |
| ca. 4.12 | (1H, d, $J_{AB} \approx 13.5$ Hz) |
| 4.16 | (1H, d, J=6.5 Hz) |
| 4.36 | (2H, broad s) |
| 5.21 | (1H, broad s) |
| 5.49 | (1H, broad s) |
| 5.77 | (1H, d, J=6.5 Hz) |
| 5.98 | (1H, s) |
| 7.26 | (1H, s) |
| ca. 7.5–7.8 | (3H, m) |
| ca. 7.9–8.1 | (2H, m) |
| 8.87 | (1H, s) |

EXAMPLE 36

1.01 g. 3'-O-Benzoylbicyclomycin was dissolved in 20 ml. N,N-dimethylformamide and 3.5 g. silver oxide and 3.5 g. methyl iodide were added thereto, whereafter the reaction mixture was stirred at ambient temperature for 8 hours. Ethyl acetate was added to the reaction mixture and insoluble material was filtered off. Ethyl acetate and water were added to the filtrate and the mixture was stirred and then the ethyl acetate layer was separated off. The layer was washed three times with water and dried over anhydrous magnesium sulphate. The solution was decolorised with active charcoal and concentrated under reduced pressure to give 0.7 g. of a pale yellowish oil which was crystallised from a mixture of n-hexane and diethyl ether to give 0.5 g. of colourless crystals of tetramethylated 3'-O-benzoylbicyclomycin; m.p. 178°–180° C.

EXAMPLE 37

5.44 g. 3'-O-Tritylbicyclomycin were dissolved in 50 ml. N,N-dimethylformamide and 1.5 g. methyl iodide and 2.35 g. silver oxide were added thereto, whereafter the mixture was stirred at ambient temperature for 10 hours. Ethyl acetate was added to the reaction mixture and the mixture was filtered. Ethyl acetate and water were added to the filtrate and the mixture was stirred. The ethyl acetate was separated and washed three times with water and then dried over anhydrous magnesium sulphate. The solution was concentrated under reduced pressure to give 6.0 g. of a pale yellowish oil which was subjected to column chromatography using silica gel. Elution was carried out with chloroform and the fractions containing the desired compound were collected. These fractions were combined and the solvent was distilled off from the solution under reduced pressure to give 4.0 g. of a colourless powder of N-(8 or 10)-methyl-3'-O-tritylbicyclomycin.

Infra-red absorption spectrum:
$\nu$cm$^{-1}$ (NaCl): 3330, 3170, 1665 (shoulder), 1650, 1590, 1200, 1145, 1060, 1035, 740.

EXAMPLE 38.

5.44 g. 3'-O-Tritylbicyclomycin were dissolved in 40 ml. N,N-dimethylformamide and 10 g. methyl iodide and 13 g. silver oxide were added thereto, whereafter the reaction mixture was stirred at ambient temperature for 7 hours. The reaction mixture was filtered and ethyl acetate and water were added to the filtrate and then the mixture was stirred. The ethyl acetate layer was separated, washed three times with water and dried over anhydrous magnesium sulphate. The solvent was distilled off from the solution under reduced pressure to give 6.0 g. of a light brown oil which was subjected to column chromatography, using silica gel. Elution was carried out with chloroform and the fractions containing the desired compound were collected. These fractions were combined and the solvent was distilled off from the solution under reduced pressure to give 5.0 g. of a colourless powder of tetramethylated 3'-O-tritylbicyclomycin.

NMR absorption spectrum: (internal standard: tetramethylsilane)

| $\delta$ppm (CDCl$_3$) | |
|---|---|
| 1.40 | (3H, s) |
| 2.10–2.40 | (2H, d) |
| 2.86 | (3H, s) |
| 3.08 | (3H, s) |
| 3.20 | (3H, s) |
| 3.24 | (3H, s) |
| 3.38–3.50 | (2H, m) |
| 4.02 | (1H, s) |
| 5.12 | (1H, m) |
| 5.60 | (1H, m) |
| 7.1–7.7 | (15H, m) |

EXAMPLE 39

1.72 g. 2-Diethylaminoethyl chloride hydrochloride was dissolved in 10 ml. N,N-dimethylformamide and 2.35 g. silver oxide were added thereto, whereafter the mixture was stirred for an hour. The mixture was filtered and the filtrate was added to 30 ml. N,N-dimethylformamide containing 5.44 g. 3'-O-tritylbicyclomycin. A further 2.35 g. silver oxide were added to the mixture and the reaction mixture was stirred at ambient temperature for 18 hours. The reaction mixture was filtered and ethyl acetate was added to the filtrate and then the solution was filtered. Ethyl acetate and water were added to the filtrate and the mixture was stirred. The ethyl acetate layer was separated and dried over anhydrous sodium sulphate. The solution was treated with activated charcoal and filtered and the solvent was distilled off from the solution under reduced pressure, whereafter the residue obtained was left to stand for a time to give 1.3 g. of crude crystals. The crystals were recrystallised from a mixture of ethyl acetate, methanol and n-hexane to give 1.0 g. of colourless crystals of N-(8 or 10)-(2-diethylaminoethyl)-3'-O-tritylbicyclomycin; m.p. 203°–204° C.

EXAMPLE 40

3.5 g. 3'-O-Tritylbicyclomycin were dissolved in 20 ml. N,N-dimethylformamide and 0.96 g. anhydrous potassium carbonate and 1.2 g. 2-iodoacetamide were added thereto, whereafter the reaction mixture was stirred at ambient temperature for 18 hours. Water and ethyl acetate were added to the reaction mixture and the mixture was stirred. The ethyl acetate layer was separated, washed three times with water and dried over anhydrous magnesium sulphate. The solvent was distilled off from the solution under reduced pressure to give a residue, which was subjected to column chromatography, using silica gel. Elution was carried out with a mixture of chloroform and ethyl acetate and the fractions containing the desired compound were collected. These fractions were combined and the solvent was distilled off from the solution under reduced pressure and the residue obtained was left to stand for a time to give 0.55 g. of crystals. The crystals were recrystallised from a mixture of chloroform and ethyl acetate to give 0.5 g. of colourless crystals of N-(8 or 10)-carbamoylmethyl-3'-O-tritylbicyclomycin; m.p. 165°–167° C.

EXAMPLE 41

1.6 g. 3'-O-Benzoylbicyclomycin was dissolved in 6 ml. N,N-dimethylformamide and 1.2 g. anhydrous potassium carbonate was added thereto, while cooling with ice-water. 1 ml. N,N-dimethylformamide containing 1.4 g. benzyl bromide was added dropwise to the mixture at the same temperature over the course of 10 minutes and then the reaction mixture was stirred at ambient temperature for 24 hours. The temperature of the mixture was slowly increased to 45° C. for 2.5 hours, while stirring. The reaction mixture was poured into ice-water and the mixture was extracted three times with ethyl acetate. The extracts were combined and washed four times with water and dried over anhydrous magnesium sulphate. The solvent was distilled off from the solution under reduced pressure to give 2.2 g. of an oily residue. The residue was solidified by adding n-hexane and the solid was collected by filtration. The solid was crystallised from a mixture of ethyl acetate and ether and the 0.69 g. of crystals obtained were recrystallised from a mixture of ethyl acetate and methanol to give 0.36 g. of colourless needles of N-(8 or 10)-benzyl-3'-O-benzoylbicyclomycin; m.p. 208°–209° C. (dec.).

Elemental analysis for $C_{26}H_{28}N_2O_8$: calculated: C 62.89%; H 5.68%; N 5.64%. found: 62.89%; 5.77%; 5.48%.

EXAMPLE 42

8.12 g. 3'-O-Benzoylbicyclomycin were dissolved in 45 ml. N,N-dimethylformamide and 6.0 g. anhydrous potassium carbonate and 5.0 g. methyl iodide were added thereto, whereafter the reaction mixture was stirred at 38° to 40° C. for 6 hours. The reaction mixture was left to stand at ambient temperature overnight, then poured into ice-water and the mixture extracted with ethyl acetate. The extract was washed four times with water and dried over anhydrous magnesium sulphate. The solvent was distilled off from the solution under reduced pressure to give 6.2 g. of a pale yellowish residue which was subjected to column chromatography using silica gel. Elution was carried out with ethyl acetate and the fractions containing the desired compound were collected. These fractions were combined and the solvent was distilled off from the solution under reduced pressure. The residue obtained was left to stand for a time to give 0.73 g. N(8), N(10)-dimethyl-3'-O-benzoylbicyclomycin.

NMR absorption spectrum:
(internal standard: tetramethylsilane)

| δppm ((CD$_3$)$_2$SO) | |
| --- | --- |
| 1.16 | (3H, s) |
| ca. 1.90–2.60 | (2H, broad m) |
| 2.76 | (3H, s) |
| 3.02 | (3H, s) |
| ca. 3.65–4.00 | (2H, broad m) |
| ca. 4.13 | (1H, d, $J_{AB} \approx$ 11.5 Hz) |
| 4.31 | (1H, d, J $\approx$ 10 Hz) |
| ca. 4.32 | (1H, d, $J_{AB} \approx$ 11.5 Hz) |
| 4.90 | (1H, s) |
| ca. 5.19 | (1H, broad s) |
| ca. 5.48 | (1H, broad s) |
| 5.95 | (1H, d, J=10 Hz) |
| 7.22 | (1H, s) |
| ca. 7.45–7.70 | (3H, m) |
| ca. 7.90–8.13 | (2H, m) |

EXAMPLE 43

3.2 g. 3'-O-Benzoylbicyclomycin were dissolved in 65 ml. dry acetone and 2.8 g. anhydrous potassium carbonate and 2.9 g. methyl iodide were added thereto, whereafter the reaction mixture was heated under reflux for 26 hours. The reaction mixture was filtered and the solvent was distilled off from the filtrate under reduced pressure to give a residue. Water and ethyl acetate were added to the residue and the mixture was stirred. The ethyl acetate layer was separated and the remaining aqueous layer was extracted with ethyl acetate. This extract and the ethyl acetate layer obtained above were combined, washed with water and dried over anhydrous magnesium sulphate. The solvent was distilled off from the solution under reduced pressure to give 1.7 g. of an oily residue which was subjected to column chromatography using silica gel. Elution was carried out with a mixture of chloroform and methanol (volume ratio 100:1) and the fractions containing the desired compound were collected. These fractions were combined and the solvent was distilled off from the solution under reduced pressure to give 1.1 g. of an oily material. The oily material was recrystallised from a mixture of ethyl acetate and diisopropyl ether to give 0.63 g. of colourless crystals of N-(8 or 10)-methyl-3'-O-benzoylbicyclomycin; m.p. 166°–168° C.

Elemental analysis for $C_{20}H_{24}N_2O_8$ calculated: C 57.13%; H 5.75%; N 6.66%. found: 57.16%; 6.05%; 6.38%.

EXAMPLE 44

3.0 g. Bicyclomycin were dissolved in 18 ml. N,N-dimethylformamide and 1.3 g. anhydrous potassium carbonate and 1.5 g. methyl iodide were added thereto, whereafter the reaction mixture was stirred at ambient temperature for 24 hours. 25 ml. ethanol were added to the reaction mixture and the mixture then filtered. The filtrate was concentrated under reduced pressure to give a residue to which 25 ml. ethanol were added. Diethyl ether was added to the ethanol solution to give a precipitate. The precipitate was washed with diethyl ether and the washings were concentrated under reduced pressure to give a residue which was treated with diethyl ether to recover the precipitate. This precipitate and the precipitate obtained above were combined to give 1.8 g. of a crude powder. 0.9 g. of the powder was subjected to column chromatography using silica gel. Elution was carried out with a mixture of chloroform and methanol (volume ratio 100:3) and the fractions containing the desired compound were collected. These fractions were combined and the solvent was distilled off from the solution under reduced pressure to give 0.55 g. of a colourless powder of N-(8 or 10)-methylbicyclomycin.

NMR absorption spectrum: (internal standard: sodium 2,2-dimethyl-2-silapentane-sulphonate)

| $\delta$ppm (D$_2$O) | |
|---|---|
| 1.36 | (3H, s) |
| ca. 2.0–2.8 | (2H, m) |
| 2.89 | (3H, s) |
| ca. 3.5–4.1 | (2H, m) |
| ca. 3.51 | (1H, d, $J_{AB} \approx$ 12 Hz) |
| ca. 3.78 | (1H, d, $J_{AB} \approx$ 12 Hz) |
| 4.16 | (1H, broad s) |
| 5.37 | (1H, broad s) |
| 5.58 | (1H, s) |

EXAMPLE 45

N-(8 or 10)-Allylbicyclomycin was obtained in substantially similar manner as described in Example 44, using bicyclomycin as starting material and allyl bromide as alkylating agent.

EXAMPLE 46

N-(8 or 10)-Propynylbicyclomycin was obtained in substantially similar manner as described in Example 44, using bicyclomycin as a starting material and propynyl bromide as alkylating agent.

EXAMPLE 47

4.0 g. 3'-O-Trityl-N-(8 or 10)-methylbicyclomycin were dissolved in a mixture of 20 ml. acetic acid and 20 ml. water and the reaction mixture was left to stand overnight at ambient temperature. The precipitated crystals of trityl alcohol were filtered off and the solvent was distilled off from the filtrate under reduced pressure to give 1.8 g. of a residue which was subjected to column chromatography using silica gel. Elution was carried out with a mixture of chloroform and acetone and the fractions containing the desired compound were collected. These fractions were combined and the solvent was distilled off from the solution under reduced pressure to give 1.5 g. N-(8 or 10)-methylbicyclomycin.

NMR absorption spectrum: (internal standard: sodium 2,2-dimethyl-2-silapentane-sulphonate)

| $\delta$ppm (D$_2$O) | |
|---|---|
| 1.35 | (3H, s) |
| ca. 2.17–2.72 | (2H, broad m) |
| 2.98 | (3H, s) |
| ca. 3.53 | (1H, d, $J_{AB} \approx$ 11.5 Hz) |
| ca. 3.73 | (1H, d, $J_{AB} \approx$ 11.5 Hz) |
| ca. 3.7–4.0 | (2H, broad m) |
| 4.16 | (1H, s) |
| 5.37 | (1H, broad s) |
| 5.58 | (1H, broad s) |

EXAMPLE 48

5.0 g. N-(8 or 10)-Methyl-1',2',6-O,O,O-trimethyl-3'-O-tritylbicyclomycin were dissolved in a mixture of 20 ml. acetic acid and 20 ml. water and the reaction mixture was left to stand overnight. The precipitated crystals of trityl alcohol were filtered off and the solvent was distilled off from the filtrate under reduced pressure to give a residue which was washed with an aqueous sodium bicarbonate solution. Ethyl acetate was added to the residue and the solution was dried. The solution was evaporated to dryness to give 800 mg. of an oily material. The oily material was crystallised from ether to give 700 mg. crystals of N-(8 or 10)-methyl-1',2',6-O,O,O-trimethylbicyclomycin; m.p. 115°–116° C.

EXAMPLE 49

3.2 g. of carbon tetrachloride containing 0.32 g. bromine were added dropwise to a mixture of 0.60 g. bicyclomycin, 0.17 g. anhydrous sodium acetate and 12 ml. acetic acid in the course of 3 hours and the reaction mixture was stirred at 16°–18° C. for an hour. 50 ml. n-hexane were added to the reaction mixture, while stirring, and the upper layer was decanted off. The residue obtained was brought to powder form with diethyl ether and extracted three times with hot 20 ml. amounts of acetone. The extracts were combined and dried over anhydrous magnesium sulphate. The solvent was distilled off from the solution under reduced pressure to give 0.90 g. colourless oily material. The oily material was crystallised from chloroform and washed with chloroform to give 0.75 g. amorphous 5,11-dibromo-5,11-dihydrobicyclomycin.

NMR absorption spectrum: (internal standard: sodium 2,2-dimethyl-2-silapentane-sulphonate)

| $\delta$ppm (D$_2$O) | |
|---|---|
| 1.38 | (3H, s) |
| ca. 2.50–2.90 | (2H, m) |
| 3.73 | (2H, s) |
| ca. 3.90–4.40 | (2H, m) |
| 4.13 | (1H, s) |
| ca. 4.08 (1H) | |
| ca. 4.37 (1H) | ($J_{AB} \approx$ 10.5 Hz) |

EXAMPLE 50

Using 1.6 g. 3'-O-benzoylbicyclomycin as a starting compound, 0.64 g. bromine as a halogenating agent and 75 ml. methylene chloride as a solvent, a reaction period of 6 hours and working up substantially as described in Example 49, a residue was obtained which was brought to a powder with diethyl ether. The powder was purified by reprecipitation to give 1.8 g. colourless amorphous 5,11-dibromo-5,11-dihydro-3'-O-benzoylbicyclomycin; m.p. 137°–139° C. (dec.).

NMR absorption spectrum: (internal standard: tetramethylsilane)

| δppm ((CD₃)₂CO) | |
| --- | --- |
| 1.52 | (3H, s) |
| 2.30–2.60 | (2H, m) |
| 3.86–4.10 | (2H, m) |
| ca. 4.07 | (1H, d, J ≈ 3 Hz) |
| 4.19 | (2H, s) |
| 4.37 | (1H, s) |
| ca. 4.46 | (1H, d, J ≈ 3 Hz) |
| 7.41–7.59 | (3H, m) |
| 7.95–8.15 | (2H, m) |

EXAMPLE 51

9.3 g. 3′-O-Benzoylbicyclomycin were suspended in 180 ml. anhydrous methylene chloride and 11.8 g. m-chloroperbenzoic acid were added thereto, whereafter the reaction mixture was heated under reflux for 20 hours, while stirring. The solvent was distilled off from the reaction mixture under reduced pressure and the residue obtained was brought to a powder with 200 ml. diethyl ether. The powder was recrystallised from ethyl acetate to give 7.5 g. of colourless prisms of 3′-O-benzoyl-5,11-epoxy-bicyclomycin; m.p. 203°–205° C. (dec.).

Elemental analysis for $C_{19}H_{22}N_2O_9$: calculated: C 54.02%; H 5.25%; N 6.63%. found: 53.77%; 5.22%; 6.42%.

EXAMPLE 52

15 g. Bicyclomycin were dissolved in a mixture of 45 ml. water and 90 ml. acetic acid and a catalytic amount of sodium tungstate monohydrate was added thereto, whereafter the mixture was cooled on an ice-bath. 6.0 g. of 30% aqueous hydrogen peroxide solution were added to the mixture, with stirring, and the reaction mixture was stirred for 24 hours at ambient temperature. The reaction mixture was washed with 200 ml. diethyl ether and the remaining aqueous solution was lyophilised. The residue was dissolved in 150 ml. acetone and the solution was left to stand overnight. The precipitated crystals were filtered off to give 1.0 g. of colourless prisms of 5,11-epoxybicyclomycin containing one mol acetone of crystallisation; m.p. 173°–174° C. (dec.).

EXAMPLE 53

2.9 g. of a colourless crystalline powder of 3′-O-butyryl-5,11-epoxybicyclomycin were obtained in substantially the same manner as described in Example 51, using 3.6 g. 3′-O-butyrylbicyclomycin as a starting material, and 5.5 g. m-chloroperbenzoic acid as an oxidising agent; m.p. 154°–156° C. (dec.).

EXAMPLE 54

0.66 g. of colourless prisms of 5,11-epoxy-2′,3′-O,O-isopropylidenebicyclomycin was obtained in substantially the same manner as described in Example 51, using 1.03 g. 2′,3′-O,O-isopropylidenebicyclomycin as a starting compound and 0.91 g. m-chloroperbenzoic acid as an oxidising agent; m.p. 181°–186° C. (dec).

Elemental analysis for $C_{15}H_{22}N_2O_8$: calculated: C 50.27%; H 6.19%; N 7.82%. found: 50.12%; 6.12%; 7.62%.

EXAMPLE 55

2.04 g. 1′,3′-O,O-Dibenzoylbicyclomycin were dissolved in 25 ml. N,N-dimethylformamide and 608 mg. methyl iodide and 928 mg. silver oxide were added thereto, whereafter the reaction mixture was stirred at ambient temperature for 12 hours. Ethyl acetate was added to the reaction mixture and the mixture was filtered. A mixture of ethyl acetate and water was added to the filtrate and the ethyl acetate layer was separated. The layer was washed three times with water and then dried over anhydrous magnesium sulphate. The solvent was distilled off from the solution under reduced pressure to give 2.0 g. of a residue which was subjected to column chromatography using silica gel. The fractions containing the desired compound were collected and combined. The solvent was distilled off from the solution under reduced pressure to give 900 mg. of a colourless powder. The powder was recrystallised from a mixture of benzene and n-hexane to give 800 mg. of colourless crystals of 1′,3′-O,O-dibenzoyl-N-(8 or 10)-methylbicyclomycin; m.p. 109°–111° C.

What we claim is:
1. 2′,3′-O,O-isopropylidenebicyclomycin.
2. 5,11-dibromo-5,11-dihydrobicyclomycin.

* * * * *

UNITED STATES PATENT AND TRADEMARK OFFICE
CERTIFICATE OF CORRECTION

PATENT NO. : 4,215,043
DATED : July 29, 1980
INVENTOR(S) : Takashi Kamiya et al.

It is certified that error appears in the above—identified patent and that said Letters Patent is hereby corrected as shown below:

Col. 6, lines 21-25, " 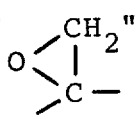 " should read -- 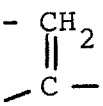 --.

Col. 6, line 51, "$R_{a1}$" should read -- $R_{d1}$ --.
Col. 11, line 16, "aliphaic" should read -- aliphatic --.
Col. 11, line 18, "cycloalkane" should read -- cycloalkene --.
Col. 11, line 19, "cyclohexane" should read -- cyclohexene --.
Col. 11, line 20, "drocarbn" should read -- drocarbon --.
Col. 12, line 3, "are" should read -- and --.
Col. 15, line 58, "trifluoroperaetic" should read -- trifluoroperacetic --.
Col. 19, line 16, "8g" should read -- 18g --.
Col. 19, line 37, "solution" should read -- sodium --.
Col. 25, line 11, "thioacetate" should read -- thioacetic --.
Col. 27, line 50, "crystallised" should read -- recrystallised --.
Col. 31, line 31, "3.6" should read -- 3.5 --.

Signed and Sealed this

Eighteenth Day of November 1980

[SEAL]

Attest:

SIDNEY A. DIAMOND

Attesting Officer

Commissioner of Patents and Trademarks